(12) United States Patent  
Niijima et al.

(10) Patent No.: US 8,410,277 B2
(45) Date of Patent: Apr. 2, 2013

(54) METHOD FOR MANUFACTURING HETEROCYCLE SUBSTITUTED PYRIDINE DERIVATIVES

(75) Inventors: Jun Niijima, Tsukuba (JP); Kazuhiro Yoshizawa, Kamisu (JP); Yuki Kosaka, Kamisu (JP); Shinya Abe, Tsukuba (JP)

(73) Assignee: Eisai R&D Managment Co., Ltd., Tokyo (JP)

( * ) Notice: Subject to any disclaimer, the term of this patent is extended or adjusted under 35 U.S.C. 154(b) by 74 days.

(21) Appl. No.: 12/809,011

(22) PCT Filed: Dec. 25, 2008

(86) PCT No.: PCT/JP2008/073545
§ 371 (c)(1),
(2), (4) Date: Jul. 2, 2010

(87) PCT Pub. No.: WO2009/081970
PCT Pub. Date: Jul. 2, 2009

(65) Prior Publication Data
US 2011/0263845 A1 Oct. 27, 2011

Related U.S. Application Data

(60) Provisional application No. 61/016,791, filed on Dec. 26, 2007.

(51) Int. Cl.
*C07D 413/14* (2006.01)
(52) U.S. Cl. .................................................. 546/256
(58) Field of Classification Search ............... 546/256, 546/272.1
See application file for complete search history.

(56) References Cited

U.S. PATENT DOCUMENTS

| | | | |
|---|---|---|---|
| 5,444,050 | A | 8/1995 | Kogan et al. |
| 5,541,185 | A | 7/1996 | Leyendecker et al. |
| 5,827,887 | A | 10/1998 | Gourvest et al. |
| 6,200,975 | B1 | 3/2001 | Carling et al. |
| 7,223,777 | B2 | 5/2007 | Sankaranarayanan |
| 7,977,485 | B2 | 7/2011 | Luithle et al. |
| 2003/0220516 | A1 | 11/2003 | Haber et al. |
| 2005/0118209 | A1 | 6/2005 | Jentszch et al. |
| 2006/0160877 | A1 | 7/2006 | Luithle et al. |
| 2007/0105904 | A1 | 5/2007 | Tanaka et al. |
| 2007/0105943 | A1 | 5/2007 | Nakamoto et al. |
| 2007/0167493 | A1 | 7/2007 | Sankaranarayanan |
| 2008/0166765 | A1 | 7/2008 | Tsukahara et al. |
| 2008/0275244 | A1 | 11/2008 | Niijima et al. |
| 2011/0263591 | A1 | 10/2011 | Luithle et al. |

FOREIGN PATENT DOCUMENTS

| | | | |
|---|---|---|---|
| EP | 0377892 | A1 | 7/1990 |
| EP | 1046640 | A2 | 10/2000 |
| EP | 1046640 | A3 | 7/2002 |
| GB | 2276161 | A | 9/1994 |
| JP | 2001-525802 | A | 12/2001 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*

(Continued)

*Primary Examiner* — Patricia L Morris
(74) *Attorney, Agent, or Firm* — Birch, Stewart, Kolasch & Birch, LLP

(57) ABSTRACT

It is an object of the present invention to provide an efficient method for manufacturing heterocycle-substituted pyridine derivatives. The present invention provides a method for manufacturing a compound represented by the following formula (I):

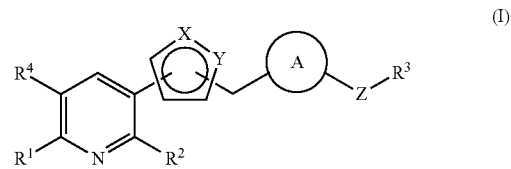

the method including reacting a compound represented by the following formula (III):

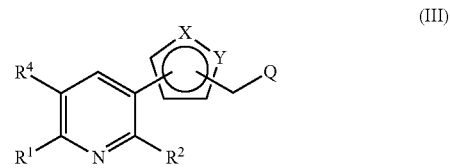

and a compound represented by the following formula (II):

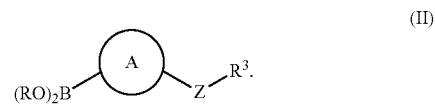

in a solvent and in the presence of a palladium catalyst and a base, wherein $R^1$ represents a hydrogen atom, etc.; $R^2$ represents a hydrogen atom, a $C_{1-6}$ alkyl group, an amino group that may be protected with a protective group, etc.; one of X and Y represents a nitrogen atom and the other represents a nitrogen atom or an oxygen atom; Q represents a leaving group; the ring A represents a 5- or 6-member heteroaryl ring or a benzene ring, which may have one or two halogen atoms or $C_{1-6}$ alkyl groups; Z represents a single bond, a methylene group, an ethylene group, an oxygen atom, etc.; R represents a hydrogen atom or a $C_{1-6}$ alkyl group, etc.; $R^3$ represents a hydrogen atom or a halogen atom, etc.; and $R^4$ represents a hydrogen atom or a halogen atom;

provided that when Z represents a single bond, or when $R^3$ represents a hydrogen atom, then $R^1$, $R^2$, and $R^4$ cannot all be a hydrogen atom at the same time.

7 Claims, No Drawings

FOREIGN PATENT DOCUMENTS

| | | |
|---|---|---|
| JP | 2005-533052 A | 11/2005 |
| JP | 2006-248938 A | 9/2006 |
| RU | 2 291 154 C2 | 1/2007 |
| WO | WO 98/50385 A1 | 11/1998 |
| WO | WO-02/04626 A1 | 1/2002 |
| WO | WO 03/002118 A1 | 1/2003 |
| WO | WO 03/059312 A2 | 7/2003 |
| WO | WO 03/099805 A1 | 12/2003 |
| WO | WO 03/104227 A1 | 12/2003 |
| WO | WO 04/000814 A1 | 12/2003 |
| WO | WO 2004/099171 A2 | 11/2004 |
| WO | WO 2004/100947 A2 | 11/2004 |
| WO | WO-2005/033079 A1 | 4/2005 |
| WO | WO 2006/138695 A1 | 12/2006 |
| WO | WO-2007/052615 A1 | 5/2007 |
| WO | WO 2008/008539 A2 | 1/2008 |
| WO | WO 2008/009078 A2 | 1/2008 |
| WO | WO 2008/019357 A2 | 2/2008 |
| WO | WO 2008/023248 A2 | 2/2008 |
| WO | WO 2008/103277 A2 | 8/2008 |
| WO | WO-2008/136279 A1 | 11/2008 |
| WO | WO 2008/141020 A1 | 11/2008 |
| WO | WO 2009/071504 A1 | 6/2009 |
| WO | WO 2010/081145 A1 | 7/2010 |

OTHER PUBLICATIONS

A Russian Office Action, dated Oct. 5, 2010, for Russian Application No. 2010125902.

Response, dated Dec. 7, 2010, in Russian Application No. 2010125902.

Official Action for corresponding Russian Patent Application No. 2010125902, dated Dec. 20, 2011.

English translation of International Preliminary Report on Patentability (Form PCT/IB/338 and 373) and of Written Opinion of the International Searching Authority (Form PCT/ISA/237) issued on Jul. 29, 2010 in PCT/JP2008/073545.

First Office Action for corresponding Chinese Patent Application No. 200880123026.8, dated Feb. 16, 2012.

Bose, D.S. et al, "Lewis Acid-Mediated Selective Removal of N-tert-Butoxycarbonyl Protective Group (t-Boc)", Synthesis, 1999, No. 1, p. 66-68.

Dilbeck, G.A. et al, "Biologically Oriented Organic Sulfur Chemistry. 19. Synthesis and Properties of 2-Amino-5-mercapto-5-methylhexanoic Acid, a Bishomologue of Penicillamine. Use of Boron Trifluoride Etherate for Catalyzing Markownikoff Addition of a Thiol to an Olefin", J. Org. Chem., 1978, vol. 43, No. 24, p. 4593-4596.

Matteson, D.S., "Boronic Esters in Stereodirected Synthesis", Tetrahedron, 1989, vol. 45, No. 7, p. 1859-1885.

Chang, K.Y. et al, "Synthesis and structure-activity relationships of quaternary ammonium cephalosporins with 3-pyrazolylpyridinium derivatives", Bioorganic & Medicinal Chemistry Letters, 2000, vol. 10, No. 11, p. 1211-1214.

Lukevics, E. et al, "Synthesis and cytotoxicity of silyl- and carbonyl-substituted isoxazoles", Chemistry of Heterocyclic Compounds, 2000, vol. 36, No. 10, p. 1226-1231.

Plate, R. et al, "Synthesis and Muscarinic Activities of 3-(Pyrazolyl)-1,2,5,6-tetrahydropyridine Derivatives", Bioorganic and Medicinal Chemistry, 1996, vol. 4, No. 2, p. 227-37.

Vrzheshch, P.V. et al, "Supercooperativity in platelet aggregation: Substituted pyridyl isoxazoles, a new class of supercooperative platelet aggregation inhibitors", FEBS Letters, 1994, vol. 351, No. 2, p. 168-170.

Lo, L. et al, "Development of highly selective and sensitive probes for hydrogen peroxide", Chemical Communications (Cambridge, United Kingdom), 2003, No. 21, p. 2728-2729.

International Search Report, dated Mar. 31, 2009, corresponding to international application PCT/JP2008/073545.

Ambinter, Accession No. 0081445172, Online Database Chemcats, Ambinter Stock Screening Collection, Jan. 1, 2012, 1 page, XP002674525.

Ambinter, Accession No. 0084551168, Online Database Chemcats, Ambinter Stock Screening Collection, Jan. 1, 2012, 1 page, XP002674524.

Ambinter, Accession No. 0090690233, Online Database Chemcats, Ambinter Stock Screening Collection, Jan. 1, 2012, 1 page, XP002674529.

Aurora Fine Chemicals LLC., Accession No. 0103856105, Online Database Chemcats, Aurora Building Blocks, Jan. 30, 2012, 1 page, XP002674532.

Bio-Vin Research Laboratories, Accession No. 2082324366, Online Database Chemcats, Bio-Vin Research Laboratories Product List, Mar. 16, 2012, 1 page, XP002674523.

Chemdiv, Inc., Accession No. 2038881093, Online Database Chemcats, ChemDiv Screening Collection, Feb. 13, 2012, 1 page, XP002674526.

Extended European Search Report for Application No. 08863620.4 dated Jun. 13, 2012.

Palmer et al., "Structure-activity relationships for 2-anilino-6-phenylpyrido[2,3-d]pyrimidin-7(8H)-ones as inhibitors of the cellular checkpoint kinase Wee1", Bioorganic & Medicinal Chemistry Letters, vol. 15, 2005, pp. 1931-1935, XP002674519.

Takahashi et al., "Alkynes as activators in the nickel-catalysed addition of organoboronates to aldehydes", Chem. Commun., 2005, pp. 1459-1461, XP002674517.

Torssell, "Zur Kenntnis der Arylborsauren. III, Bromierung der Tolylborsauren nach Wohl-Ziegler", Arkiv for Kemi, vol. 10, No. 36, Sep. 12, 1956, pp. 507-511, XP002674521.

Response to the Official Action for corresponding Russian Patent Application No. 2010125902, dated Jun. 21, 2012.

Response to Chinese Office Action for Application No. 200880123026.8 dated Jun. 28, 2012 (with English translation).

Notification of 2nd Office Action for corresponding Chinese Patent Application No. 200880123026.8, dated Sep. 11, 2012.

Decision on Grant of a Patent for Invention for corresponding Russian Patent Application No. 2010125902, dated Aug. 15, 2012.

Response to Office Action for corresponding Chinese Patent Application No. 200880123026.8, dated Nov. 22, 2012.

Response to Office Action for corresponding European Patent Application No. 08863620.4, dated Dec. 14, 2012.

Notification of the 3rd Office Action for corresponding Chinese Patent Application No. 200880123026.8, dated Dec. 24, 2012.

* cited by examiner

METHOD FOR MANUFACTURING HETEROCYCLE SUBSTITUTED PYRIDINE DERIVATIVES

This application is the National Phase of PCT/JP2008/073545 filed on Dec. 25, 2008, which claims priority under 35 U.S.C. 119(e) to U.S. Provisional Application No. 61/016,791 filed on Dec. 26, 2007, all of which are hereby incorporated by reference into the present application.

TECHNICAL FIELD

This invention relates to a method for manufacturing heterocycle-substituted pyridine derivatives.

BACKGROUND ART

In recent years, managements of opportunistic infections have become more and more significant more than ever because of an increase in the number of elderly people and immunocompromised patients as a result of advanced chemotherapies or the like. As demonstrated by the fact that opportunistic infections are occurring one after another by different a virulent pathogen, it has been shown that the problem of infectious disease will not ends as long as there are underlying diseases that diminish the immune functions of patients. Consequently, new strategies for infectious diseases control, including the problem of drug-resistant pathogen, will be one of the important issues in the soon-to-come aged society.

In the field of antifungal agents, heretofore, for instance, amphotericine B which is based on a polyene skeleton, fluconazole, itraconazole and voriconazole which are based on an azole skeleton, or the like, have been developed for the treatment of deep seated mycoses. Most of pre-existing drugs already available commercially have similar mechanism of action, and currently, the appearance of azole-resistant fungi or the like has been problems.

In recent years, as a 1,3-β-glucan synthetase inhibitor with a novel mechanism, naturally occurring compound-derived cyclic hexapeptides caspofungin and micafungin or the like, have been developed; however, from the fact that these agents only exist in injectable form, they are not yet sufficient practically as antifungal agents.

Since there have been the situations that the pre-existing antifungal agents are insufficient for treatment of the deep seated mycoses, there is a demand and need for development of agents which are based on a novel mechanism and are of high safety.

As the related art relevant to antifungal agents based on such a novel mechanism, Patent Documents 1 and 2 describe pyridine derivatives which demonstrates effects against the onset, progress, and persistence of infections by inhibiting the expression of cell wall proteins, inhibiting the cell wall assembly and also adhesion onto cells, and preventing pathogens from showing pathogenicity, with the process which transports GPI (Glycosylphosphatidylinositol)-anchored proteins to the cell wall being inhibited.

In light of this situation, there has been proposed in Patent document 3 a hetero ring-substituted pyridine derivative as an antifungal agent that has excellent antifungal action not seen in conventional antifungal agents, and is also superior in terms of its properties, safety, and metabolic stability.

Patent Document 1: WO 02/04626
Patent Document 2: WO 05/033079
Patent Document 3: WO 07/052615

DISCLOSURE OF INVENTION

Problems to be Solved by the Invention

It is an object of the present invention to provide an efficient method for manufacturing heterocycle-substituted pyridine derivatives, and to provide an intermediate that is useful in the manufacture of the heterocycle-substituted pyridine derivatives.

Means for Solving the Problems

As a result of diligent research aimed at solving the above problem, the inventors arrived at the present invention upon discovering an efficient method for manufacturing heterocycle-substituted pyridine derivatives by using a specific coupling reaction.

Specifically, in a first aspect of the present invention, there are provided:

[1] A method for manufacturing a compound represented by the following formula (I):

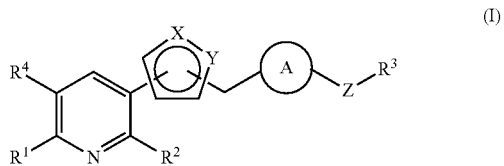

the method comprising reacting a compound represented by the following formula (III):

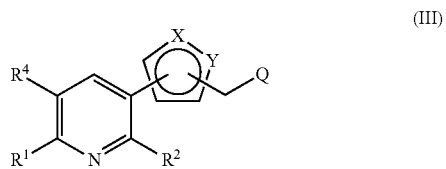

and a compound represented by the following formula (II):

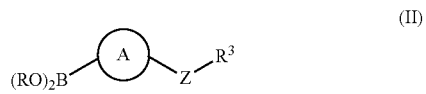

in a solvent and in the presence of a palladium catalyst and a base, wherein $R^1$ represents a hydrogen atom, a halogen atom, an amino group, $R^{11}$—NH— (wherein $R^{11}$ represents a $C_{1-6}$ alkyl group, a hydroxy $C_{1-6}$ alkyl group, a $C_{1-6}$ alkoxy $C_{1-6}$ alkyl group, or a $C_{1-6}$ alkoxycarbonyl $C_{1-6}$ alkyl group), $R^{12}$—(CO)—NH— (wherein $R^{12}$ represents a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group, or a $C_{1-6}$ alkoxy $C_{1-6}$ alkyl group;

$R^2$ represents a hydrogen atom, a $C_{1-6}$ alkyl group, an amino group that may be protected with a protective group, or a di-$C_{1-6}$ alkylamino group;

one of X and Y represents a nitrogen atom and the other represents a nitrogen atom or an oxygen atom;

Q represents a leaving group;

the ring A represents a 5- or 6-member heteroaryl ring or a benzene ring, which may have one or two halogen atoms or $C_{1-6}$ alkyl groups;

Z represents a single bond, a methylene group, an ethylene group, an oxygen atom, a sulfur atom, —CH$_2$O—, —OCH$_2$—, —NH—, —CH$_2$NH—, —NHCH$_2$—, —CH$_2$S—, or —SCH$_2$—;

R represents a hydrogen atom or a C$_{1-6}$ alkyl group, if the two R groups are both C$_{1-6}$ alkyl groups, they may together form a ring;

R$^3$ represents a hydrogen atom or a halogen atom, or a C$_{1-6}$ alkyl group, a C$_{3-8}$ cycloalkyl group, a C$_{6-10}$ aryl group, a 5- or 6-member heteroaryl group, or a 5- or 6-member non-aromatic heterocyclic group, wherein these groups may have one or two substituents selected from a substituent group α; and R$^4$ represents a hydrogen atom or a halogen atom;

provided that when Z represents a single bond, or when R$^3$ represents a hydrogen atom, then R$^1$, R$^2$, and R$^4$ cannot all be a hydrogen atom at the same time,

[substituent group α]

a halogen atom, a cyano group, a C$_{1-6}$ alkyl group, a C$_{1-6}$ alkoxy group, a C$_{1-6}$ alkoxycarbonyl group, a C$_{3-8}$ cycloalkyl group, a C$_{2-6}$ alkenyl group, and a C$_{2-6}$ alkynyl group.

[2] The manufacturing method according to item [1] above, wherein the Q in the above formula (III) represents a halogen atom or a substituted sulfonyloxy group.

[3] The manufacturing method according to item [1] or [2] above, wherein a partial structure represented by:

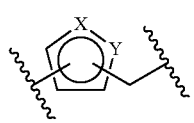

(IV)

in the above formula (I) is the following partial structure:

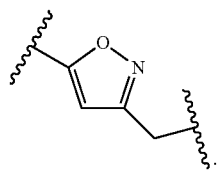

(V)

[4] The manufacturing method according to any of items [1] to [3] above, wherein when the R$^2$ is an amino group that may be protected with a protective group, the method further comprises deprotecting the protective group.

[5] The manufacturing method according to any of items [1] to [4] above, wherein the compound represented by the following formula (III):

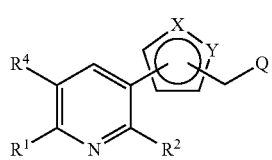

(III)

Is manufactured by a manufacturing method comprising the steps of subjecting a compound represented by the following formula (VI):

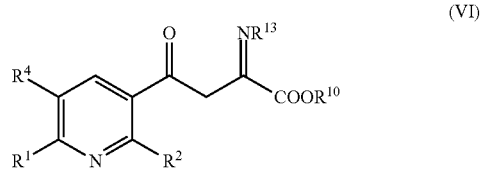

(VI)

to a cyclization reaction;
performing a reduction reaction; and
performing halogenation thereafter,
(wherein R$^1$, R$^2$, R$^4$, X, Y, and Q are defined the same as above,
R$^{10}$ represents a hydrogen atom or a C$_{1-6}$ alkyl group, and
R$^{13}$ represents a hydroxyl group or a C$_{1-6}$ alkyl group).

[6] The manufacturing method according to item [5] above, wherein when the R$^2$ represents an amino group having a protective group, the method further comprises deprotecting the protective group after the reduction reaction.

[7] The manufacturing method according to item [5] or [6] above, wherein when the R$^2$ represents an amino group, the method further comprises protecting the amino group.

In a second aspect of the present invention, there is also provided:

[8] a compound represented by the following formula (VII) or a salt thereof:

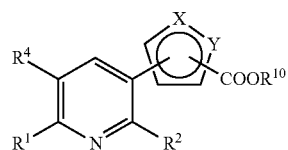

(VII)

wherein
R$^1$ represents a hydrogen atom, a halogen atom, an amino group, R$^{11}$—NH— (wherein R$^{11}$ represents a C$_{1-6}$ alkyl group, a hydroxy C$_{1-6}$ alkyl group, a C$_{1-6}$ alkoxy C$_{1-6}$ alkyl group, or a C$_{1-6}$ alkoxycarbonyl C$_{1-6}$ alkyl group), R$^{12}$—(CO)—NH— (wherein R$^{12}$ represents a C$_{1-6}$ alkyl group or a C$_{1-6}$ alkoxy C$_{1-6}$ alkyl group), a C$_{1-6}$ alkyl group, a hydroxy C$_{1-6}$ alkyl group, a cyano C$_{1-6}$ alkyl group, a C$_{1-6}$ alkoxy group, or a C$_{1-6}$ alkoxy C$_{1-6}$ alkyl group;

R$^2$ represents a hydrogen atom, a C$_{1-6}$ alkyl group, an amino group that may be protected with a protective group, or a di-C$_{1-6}$ alkylamino group;

one of X and Y represents a nitrogen atom and the other represents a nitrogen atom or an oxygen atom;

R$^4$ represents a hydrogen atom or a halogen atom; and

R$^{10}$ represents a hydrogen atom or a C$_{1-6}$ alkyl group.

[9] The compound or a salt thereof according to item [8] above, wherein a partial structure represented by:

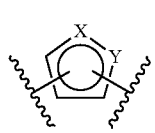

(VIII)

in the above formula (VII) is the following partial structure:

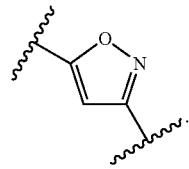
(IX)

In a third aspect of the present invention, there is further provided:

[10] A compound represented by the following formula (X) or a salt thereof:

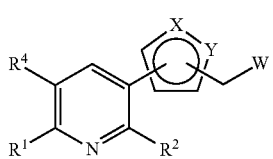
(X)

wherein $R^1$ represents a hydrogen atom, a halogen atom, an amino group, $R^{11}$—NH— (wherein $R^{11}$ represents a $C_{1-6}$ alkyl group, a hydroxy $C_{1-6}$ alkyl group, a $C_{1-6}$ alkoxy $C_{1-6}$ alkyl group, or a $C_{1-6}$ alkoxycarbonyl $C_{1-6}$ alkyl group), $R^{12}$—(CO)—NH— (wherein $R^{12}$ represents a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group, or a $C_{1-6}$ alkoxy $C_{1-6}$ alkyl group;

$R^2$ represents a hydrogen atom, a $C_{1-6}$ alkyl group, an amino group that may be protected with a protective group, or a di-$C_{1-6}$ alkylamino group;

one of X and Y represents a nitrogen atom and the other represents a nitrogen atom or an oxygen atom;

W represents a hydroxyl group, a halogen atom, or a substituted sulfonyloxy group; and $R^4$ represents a hydrogen atom or a halogen atom.

[11] The compound or a salt thereof according to item [10] above, wherein a partial structure represented by:

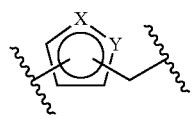
(IV)

in the above formula (X) is the following partial structure:

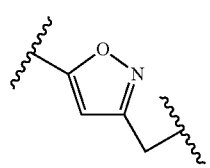
(V)

In a fourth aspect of the present invention, there is still further provided:

[12] A compound represented by the following formula (XI) or a salt thereof:

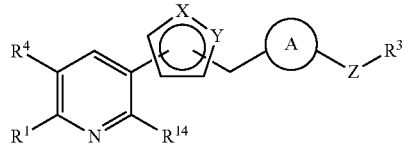
(XI)

wherein $R^1$ represents a hydrogen atom, a halogen atom, an amino group, $R^{11}$—NH— (wherein $R^{11}$ represents a $C_{1-6}$ alkyl group, a hydroxy $C_{1-6}$ alkyl group, a $C_{1-6}$ alkoxy $C_{1-6}$ alkyl group, or a $C_{1-6}$ alkoxycarbonyl $C_{1-6}$ alkyl group), $R^{12}$—(CO)—NH— (wherein $R^{12}$ represents a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group, or a $C_{1-6}$ alkoxy $C_{1-6}$ alkyl group;

$R^{14}$ represents an amino group protected with a protective group;

one of X and Y represents a nitrogen atom and the other represents a nitrogen atom or an oxygen atom;

the ring A represents a 5- or 6-member heteroaryl ring or a benzene ring, which may have one or two halogen atoms or $C_{1-6}$ alkyl groups;

Z represents a single bond, a methylene group, an ethylene group, an oxygen atom, a sulfur atom, —CH$_2$O—, —OCH$_2$—, —NH—, —CH$_2$NH—, —NHCH$_2$—, —CH$_2$S—, or —SCH$_2$—;

$R^3$ represents a hydrogen atom or a halogen atom, or a $C_{1-6}$ alkyl group, a $C_{3-8}$ cycloalkyl group, a $C_{6-10}$ aryl group, a 5- or 6-member heteroaryl group, or a 5- or 6-member non-aromatic heterocyclic group, where these groups may have one or two substituents selected from a substituent group α; and $R^4$ represents a hydrogen atom or a halogen atom;

provided that when Z represents a single bond, or when $R^3$ represents a hydrogen atom, then $R^1$ and $R^4$ cannot both be a hydrogen atom at the same time,

[substituent group α]

a halogen atom, a cyano group, a $C_{1-6}$ alkyl group, a $C_{1-6}$ alkoxy group, a $C_{1-6}$ alkoxycarbonyl group, a $C_{3-8}$ cycloalkyl group, a $C_{2-6}$ alkenyl group, and a $C_{2-6}$ alkynyl group.

[13] The compound or a salt thereof according to item [12] above, wherein a partial structure represented by:

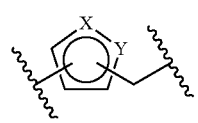
(IV)

in the above formula (XI) is the following partial structure:

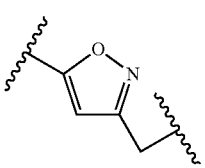
(V)

In a fifth aspect of the present invention, there is still more further provided:

[14] A compound represented by the following formula (XII) or a salt thereof:

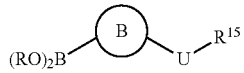

(XII)

wherein
the ring B represents a benzene ring, which may have one or two halogen atoms or $C_{1-6}$ alkyl groups;
U represents —$CH_2O$—;
R represents a hydrogen atom or a $C_{1-6}$ alkyl group, and when the two R groups are both $C_{1-6}$ alkyl groups, they may together form a ring; and
$R^{15}$ represents a hydrogen atom or a halogen atom, or a pyridine ring that may have one or two substituents selected from a substituent group α,
[substituent group α]
a halogen atom, a cyano group, a $C_{1-6}$ alkyl group, a $C_{1-6}$ alkoxy group, a $C_{1-6}$ alkoxycarbonyl group, a $C_{3-8}$ cycloalkyl group, a $C_{2-6}$ alkenyl group, and a $C_{2-6}$ alkynyl group.

Advantageous Effects of the Invention

According to the manufacturing method of the present invention, there are provided an efficient method for manufacturing heterocycle-substituted pyridine derivatives, and an intermediate that is useful in the manufacture of the heterocycle-substituted pyridine derivatives. This makes possible the manufacture of heterocycle-substituted pyridine derivatives on an industrial scale.

BEST MODE FOR CARRYING OUT THE INVENTION

The following embodiments are examples for illustrating the present invention, but these are not intended to limit the present invention to these embodiments alone. The present invention can be worked in a variety of different aspects without departing from the gist thereof.

The present invention relates to a method for manufacturing heterocycle-substituted pyridine derivatives, and a compound represented by:

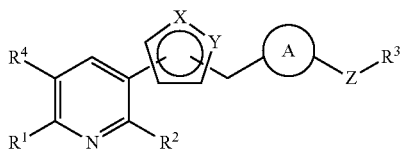

(I)

can be manufactured by reacting a compound represented by the following formula (III):

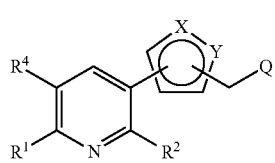

(III)

and a compound represented by the following formula (II):

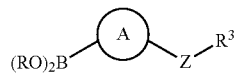

(II)

in a solvent and in the presence of a palladium catalyst and a base,
and when $R^2$ represents an amino group that may be protected with a protective group, by further deprotecting the protective group.

The ring A, $R^1$, $R^2$, $R^3$, $R^4$, X, Y, Z, Q, and R in the above formulas (I), (III), and (II) are defined the same as above.

The heterocycle-substituted pyridine derivatives obtained by the manufacturing method according to the present invention are known from WO 07/052615, which is the above-mentioned Patent Document 3, and include compounds represented by the following formula (I) and salts thereof:

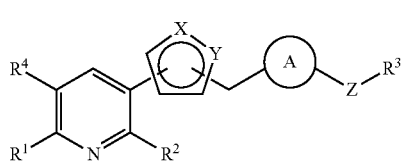

(I)

The ring A, $R^1$, $R^2$, $R^3$, $R^4$, X, Y, and Z in the above formula (I) are defined the same as above.

The present invention is explained below in more detail by reference to the symbols and the terms used herein being defined and the following examples.

Herein, a structural formula of a compound sometimes represents a certain isomer for convenience of description. However, compounds manufactured according to the manufacturing method of the present invention may include all possible isomers, such as structurally possible geometric isomers, optical isomers generated due to the presence of asymmetric carbons, stereoisomers, tautomers, and mixtures of isomers, and are not limited to formulae being used for the convenience of description, and may be either one of two isomers or a mixture of both isomers. Thus, the compounds according to the present invention may be either optically active compounds having an asymmetric carbon atom in their molecules or their racemates, and are not restricted to either of them but include both. Furthermore, the compounds according to the present invention may exhibit crystalline polymorphism, but likewise are not restricted to any one of these, but may be in any one of these crystal forms or exist as a mixture of two or more crystal forms. The compounds according to the present invention also include both anhydrous and solvates such as hydrated forms.

The term "$C_{1-6}$ alkyl group" used in the present specification refers to a straight-chain or branched-chain alkyl group with 1 to 6 carbon atoms which is a monovalent group induced by removal of any one hydrogen atom from an aliphatic hydrocarbon with 1 to 6 carbon atoms. Specifically, examples of "$C_{1-6}$ alkyl group" may include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a 1-methylbutyl group, a 2-methylbutyl group, a 1,1-dimethylpropyl group, a 1,2-dimethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2,-trimethylpropyl group, a 1,2,2-trimethylpropyl group, a 1-ethyl-1-methylpropyl group, a 1-ethyl-2-methylpropyl group or the like, preferably a methyl group, an ethyl group, a n-propyl group, an isopropyl group, a n-butyl group, an isobutyl group, a sec-butyl group or a tert-butyl group or the like, more preferably a methyl group, an ethyl group or a propyl group.

The term "$C_{2-6}$ alkenyl group" used in the present specification refers to a straight-chain or branched-chain alkenyl group with 2 to 6 carbon atoms which may contain 1 or 2 double bonds. Specifically, examples of "$C_{2-6}$ alkenyl group" may include an ethenyl group, a 1-propenyl group, a 2-propenyl group, a 1-butenyl group, a 2-butenyl group, a 3-butenyl group, a 2-methyl-1-propenyl group, a pentenyl group, a 3-methyl-2-butenyl group, a hexenyl group, a hexanedienyl group or the like, preferably an ethenyl group, a 1-propenyl group, a 2-propenyl group, a 1-butenyl group, a 2-butenyl group, a 3-butenyl group, a 2-methyl-1-propenyl group, a 3-methyl-2-butenyl group or the like.

The term "$C_{2-6}$ alkynyl group" used in the present specification refers to a straight-chain or branched-chain alkynyl chain with 2 to 6 carbon atoms which may contain 1 or 2 triple bonds. Specifically, examples of "$C_{2-6}$ alkynyl group" may include an ethynyl group, a 1-propynyl group, a 2-propynyl group, a 1-butynyl group, a 2-butynyl group, a 3-butynyl group, a pentynyl group, a hexynyl group, a hexanediynyl group or the like, preferably an ethynyl group, a 1-propynyl group, a 2-propynyl group, a 1-butynyl group, a 2-butynyl group, a 3-butynyl group or the like.

The term "$C_{3-8}$ cycloalkyl group" used in the present specification refers to a cyclic aliphatic hydrocarbon group with 3 to 8 carbon atoms. Specifically, examples of "$C_{3-8}$ cycloalkyl group" may include a cyclopropyl group, a cyclobutyl group, a cyclopentyl group, a cyclohexyl group, a cycloheptyl group, a cyclooctyl group or the like, preferably a cyclopropyl group, a cyclobutyl group, a cyclopentyl group, a cyclohexyl group or the like.

The term "$C_{1-6}$ alkoxy group" used in the present specification refers to a group in which an oxygen atom is bonded to terminus of the "$C_{1-6}$ alkyl group" defined above. Specifically, examples of "$C_{1-6}$ alkoxy group" may include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a neopentyloxy group, a 1-methylbutoxy group, a 2-methylbutoxy group, a 1,1-dimethylpropoxy group, a 1,2-dimethylpropoxy group, a n-hexyloxy group, an isohexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, a 1,2,2-trimethylpropoxy group, a 1-ethyl-1-methylpropxy group, a 1-ethyl-2-methylpropoxy group or the like, preferably a methoxy group, an ethoxy group, a n-propoxy group, an isopropoxy group, a n-butoxy group, an isobutoxy group, a sec-butoxy group, a tert-butoxy group or the like.

The term "hydroxyl $C_{1-6}$ alkyl group" used in the present specification refers to a group in which any of the hydrogen atoms in a "$C_{1-6}$ alkyl group" as defined above has been replaced with a hydroxyl group. Specifically, examples of "hydroxyl $C_{1-6}$ alkyl group" may include a hydroxymethyl group, a 1-hydroxyethyl group, a 2-hydroxyethyl group, a 1-hydroxy-n-propyl group, a 2-hydroxy-n-propyl group, a 3-hydroxy-n-propyl group, a 1-hydroxy-isopropyl group, a 2-hydroxy-isopropyl group, a 3-hydroxy-isopropyl group, a 1-hydroxy-tert-butyl group or the like, preferably a hydroxymethyl group, a 1-hydroxyethyl group, a 2-hydroxyethyl group or the like.

The term "cyano $C_1$ to $C_6$ alkyl group" used in the present specification refers to a group in which any hydrogen atom in the "$C_{1-6}$ alkyl group" defined above has been replaced with a cyano group. Specific examples of "cyano $C_1$ to $C_6$ alkyl group" include a cyanomethyl group, a 1-cyanoethyl group, a 2-cyanoethyl group, a 1-cyano-n-propyl group, a 2-cyano-n-propyl group, a 3-cyano-n-propyl group, a 1-cyano-isopropyl group, a 2-cyano-isopropyl group, a 3-cyano-isopropyl group, and a 1-cyano-tert-butyl group, preferably a cyanomethyl group, a 1-cyanoethyl group, a 2-cyanoethyl group, or the like.

The term "$C_{1-6}$ alkoxycarbonyl group" used in the present specification refers to a group in which a carbonyl group is bonded to terminus of the "$C_{1-6}$ alkoxy group" defined above. Specifically, examples of "$C_{1-6}$ alkoxycarbonyl group" may include a methoxycarbonyl group, an ethoxycarbonyl group, a n-propoxycarbonyl group, an isopropoxycarbonyl group or the like.

The term "$C_{1-6}$ alkoxycarbonyl $C_{1-6}$ alkyl group" used in the present specification refers to a group in which the "$C_{1-6}$ alkyl group" defined above is bonded to terminus of the "$C_{1-6}$ alkoxycarbonyl group" defined above. Specifically, examples of the "$C_{1-6}$ alkoxycarbonyl $C_{1-6}$ alkyl group" may include a methoxycarbonyl methyl group, a methoxycarbonyl ethyl group, an ethoxycarbonyl methyl group, an ethoxycarbonyl ethyl group or the like.

The term "$C_{6-10}$ aryl group" used in the present specification refers to an aromatic hydrocarbon cyclic group with 6 to 10 carbon atoms. Specifically, examples of "$C_{6-10}$ aryl group" may include a phenyl group, a 1-naphthyl group, a 2-naphthyl group, an indenyl group, an azulenyl group, a heptalenyl group or the like, preferably a phenyl group, a 1-naphthyl group, 2-naphthyl group or the like.

The term "$C_{1-6}$ alkoxy $C_{1-6}$ alkyl group" used in the present specification refers to a group in which any of the hydrogen atoms in a "$C_{1-6}$ alkyl group" as defined above has been replaced with a "$C_{1-6}$ alkoxy group" as defined above. Specifically, examples of "$C_{1-6}$ alkoxy $C_{1-6}$ alkyl group" may include a methoxymethyl group, an ethoxymethyl group, a n-propoxymethyl group, a methoxyethyl group, an ethoxyethyl group or the like.

The term "leaving group" used in the present specification refers to a group that acts as a leaving group during a cross-coupling reaction, and examples of "leaving group" may include a halogen atom, a substituted sulfonyloxy group or the like.

The term "halogen atom" used in the present specification refers to a fluorine atom, a chlorine atom, a bromine atom or an iodine atom.

The term "substituted sulfonyloxy group" used in the present specification refers to a sulfonyloxy group in which any one substituent is bonded to the sulfonyloxy group. Examples of substituents may include a $C_{1-6}$ alkyl group and a phenyl group which may be substituted with a halogen atom, a $C_{1-6}$ alkyl group, a nitro group, or a phenyl group. Specific examples of "substituted sulfonyloxy group" may include a para-toluenesulfonyloxy group, a benzylsulfonyloxy group, methanesulfonyloxy group, a trifluoromethanesulfonyloxy group, and a chloromethanesulfonyloxy group or the like.

The term "hetero atom" used in the present specification refers to a nitrogen atom, a sulfur atom, or an oxygen atom.

The term "5- or 6-member heteroaryl ring" used in the present specification refers to an aromatic ring in which the number of atoms making up the ring is 5 or 6, and 1 or more hetero atoms are included in the atoms making up the ring. Specifically, examples of "5- or 6-member heteroaryl ring" may include a furan ring, a thiophene ring, a pyrrole ring, a pyridine ring, a pyrazine ring, a pyridazine ring, a pyrimidine ring, a triazole ring (a 1,2,3-triazole ring, a 1,2,4-triazole ring, etc.), a tetrazole ring (a 1H-tetrazole ring, a 2H-tetrazole ring, etc.), a thiazole ring, a pyrazole ring, an oxazole ring, an isoxazole ring, an isothiazole ring, an oxadiazole ring, a thiadiazole ring or the like, preferably an isoxazole ring.

The term "5- or 6-member heteroaryl group" used in the present specification refers to a monovalent group induced by removing 1 hydrogen atom from any position in an aromatic ring in which the number of atoms making up the ring is 5 or 6 and one or more hetero atoms are included in the atoms making up the ring. Specifically, examples of "5- or 6-member heteroaryl group" may include a furyl group (a 2-furyl group or a 3-furyl group, etc.), a thienyl group (a 2-thienyl group or a 3-thienyl group, etc.), a pyrrolyl group (a 1-pyrrolyl group, a 2-pyrrolyl group or a 3-pyrrolyl group, etc.), a pyridyl group (a 2-pyridyl group, a 3-pyridyl group, a 4-pyridyl group, etc.), a pyrazinyl group, a pyridazinyl group (a 3-pyridazinyl group or a 4-pyridazinyl group, etc.), a pyrimidinyl group (a 2-pyrimidinyl group, a 4-pyrimidinyl group or a 5-pyrimidinyl group, etc.), a triazolyl froup (a 1,2,3-triazolyl group or a 1,2,4-triazolyl group, etc.), a tetrazolyl group (a 1H-tetrazolyl group or a 2H-tetrazolyl group, etc.), a thiazolyl group (a 2-thiazolyl group, a 4-thiazolyl group or a 5-thiazolyl group, etc.), a pyrazolyl group (a 3-pyrazolyl group or a 4-pyrazolyl group, etc.), an oxazolyl group (a 2-oxazolylgroup, a 4-oxazolyl group or a 5-oxazolyl group, etc.), an isoxazolyl group (a 3-isoxazolyl group, a 4-isoxazolyl group or a 5-isoxazolyl group, etc.), an isothiazolyl group (a 3-isothiazolyl group, a 4-isothiazolyl group or a 5-isothiazolyl group, etc.), an oxadiazolyl group, a thiadiazolyl group or the like.

The term "5- or 6-member non-aromatic heterocyclic group" used in the present specification refers to a monovalent group induced by removing 1 hydrogen atom from any position in a non-aromatic ring in which the number of atoms making up the ring is 5 or 6 and 1 or more hetero atoms are included in the atoms making up the ring. Specifically, examples of "5- or 6-member non-aromatic heterocyclic group" may include a pyrrolidinyl group, a piperadinyl group, a piperidinyl group, a morpholinyl group, a tetrahydrofuryl group, a tetrahydropyranyl group or the like.

The term "di $C_{1-6}$ alkylamino group" used in the present specification refers to a group in which 2 hydrogen atoms of the amino group are replaced with the "$C_{1-6}$ alkyl groups" defined above being the same as or different from each other. Specifically, examples of the term "di $C_{1-6}$ alkylamino group" may include a N, N-dimethylamino group, a N, N-diethylamino group, a N, N-di-n-propylamino group, a N, N-di-isopropylamino group, a N, N-di-n-butylamino group, a N, N-isobutylamino group, a N, N-di-sec-butylamino group, a N, N-di-tert-butylamino group, a N-ethyl-N-methylamino group, a N-n-propylamino-N-methylamino group, a N-iso-propyl-N-methylamino group, a N-n-butyl-N-methylamino group, a N-isobutyl-N-methylamino group, a N-sec-butyl-N-methylamino group, a N-tert-butyl-N-methlamino group or the like, preferably a N, N-dimethylamino group, a N, N-diethylamino group, N-ethyl-N-methylamino group or the like.

The term "may have 1 or 2 substituents" used in the specification means that there may be 1 or 2 substituents in any combination in sites capable of substituting.

$R^1$ preferably represents a hydrogen atom, a halogen atom, an amino group, a $C_{1-6}$ alkyl group, a $C_{1-6}$ alkoxy group, a $C_{1-6}$ alkylamino group, a hydroxyl $C_{1-6}$ alkylamino group, or a $C_{1-6}$ alkoxy $C_{1-6}$ alkyl group, and more preferably a hydrogen atom, an amino group or a $C_{1-6}$ alkoxy $C_{1-6}$ alkyl group, with a methoxymethyl group being preferred as the $C_{1-6}$ alkoxy $C_{1-6}$ alkyl group.

$R^2$ preferably represents a hydrogen atom, an amino group that may be protected with a protective group, or a di-$C_{1-6}$ alkylamino group, with an amino group that may be protected with a protective group being preferable. Here, the term "protective group" of the "amino group that may be protected with a protective group" is not limited to the following, but examples thereof may include carbamates such as a methoxycarbonyl group, an ethoxycarbonyl group, or a tert-butoxycarbonyl group; and amide groups such as a formyl group, an acetyl group, a pivaloyl group. When $R^2$ represents an amino group that may be protected with a protective group, then one of the hydrogens of the amino group may be protected with a protective group, or two of the hydrogens of the amino group may be protected with a protective group. The protective group of the amino group used in the manufacturing method according to the present invention preferably represents an acetyl group, a pivaloyl group, or a tert-butoxycarbonyl group, with a pivaloyl group or a tert-butoxycarbonyl group being more preferable.

One of X and Y represents a nitrogen atom while the other represents a nitrogen atom or an oxygen atom.

The partial structure represented by the following formula (IV) including X and Y:

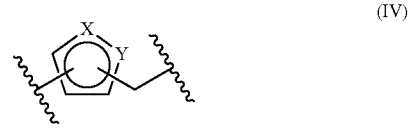

(IV)

is preferably a structure having an isoxazole skeleton represented below.

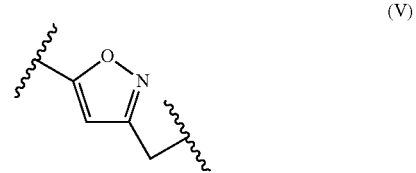 [SMILES: *Cc1cc(*)on1]

(V)

For example, in the case of the partial structure of formula (V), the structure of the compound manufactured by the manufacturing method according to the present invention will be as represented by the following formula.

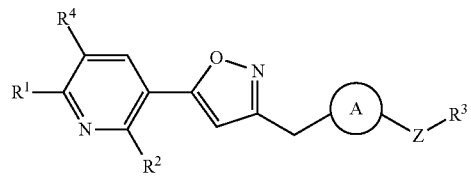

The ring A represents a 5- or 6-member heteroaryl ring or a benzene ring, which may have one or two halogen atoms or $C_{1-6}$ alkyl groups, and preferably represents a pyridine ring, a benzene ring, a furan ring, a thiophene ring, or a pyrrole ring, with a pyridine ring, a benzene ring, or a thiophene ring being more preferable, and a pyridine ring or a benzene ring being more preferable Z represents a single bond, a methylene group, an ethylene group, an oxygen atom, a sulfur atom, —CH$_2$O—, —OCH$_2$—, —NH—, —NHCH$_2$—, —CH$_2$NH—, —CH$_2$S—, or —SCH$_2$—, of which a methylene group, an oxygen atom, —CH$_2$O—, or —OCH$_2$— is preferred, with an oxygen atom, —CH$_2$O—, or —OCH$_2$— being more preferable.

$R^3$ represents a hydrogen atom or a halogen atom, or represents a $C_{1-6}$ alkyl group, a $C_{3-8}$ cycloalkyl group, a $C_{6-10}$ aryl group, or a 5- or 6-member heteroaryl group, each of which may have one or two substituents selected from a substituent group α.

[Substituent Group α]

a halogen atom, a cyano group, a $C_{1-6}$ alkyl group, a $C_{1-6}$ alkoxy group, a $C_{1-6}$ alkoxycarbonyl, a $C_{3-8}$ cycloalkyl group, a $C_{2-6}$ alkenyl group, and a $C_{2-6}$ alkynyl group Preferable examples of $R^3$ may include an n-butyl group, a cyclopropyl group, a phenyl group, a fluorophenyl group, a furyl group, a chlorofuryl group, a methylfuryl group, a thienyl group, a bromothienyl group, a methylthienyl group, a pyridyl group, and a methylpyridyl group, with an n-butyl group, a cyclopropyl group, a phenyl group, a fluorophenyl group, a pyridyl group, and a methylpyridyl group being more preferable.

Z and $R^3$ can be combined as necessary to configure substituents for the ring A. Preferable examples of $R^3$—Z— as substituents of the ring A thus configured may include a phenoxy group, a benzyloxy group, a 2-fluoro-benzyloxy group, a 3-fluoro-benzyloxy group, a 4-fluoro-benzyloxy group, a pyridin-2-yloxymethyl group, a 6-methyl-pyridin-2-yloxymethyl group, a pyridin-2-yl methoxy group, a 6-methyl-pyridin-2-ylmethoxy group, a 4-methyl-pyridin-2-ylmethoxy group, a butoxymethyl group, and a cyclopropylmethoxy group.

Preferable examples of the compounds manufactured by the manufacturing method according to the present invention may include:

3-(3-(4-benzyloxy-benzyl)isoxazol-5-yl)-pyridin-2-ylamine;
3-(3-(4-pyridin-2-yloxymethyl)-benzyl)-isoxazol-5-yl)-pyridin-2-ylamine;
3-(3-(4-pyridin-2-ylmethoxy)-benzyl)-isoxazol-5-yl)-pyridin-2-ylamine;
3-(3-(4-(4-methyl-pyridin-2-ylmethoxy)-benzyl)-isoxazol-5-yl)-pyridin-2-ylamine;
3-(3-(6-benzyloxy-pyridin-3-ylmethyl)-isoxazol-5-yl)-pyridin-2-ylamine;
3-(3-(4-benzyloxy-benzyl)-isoxazol-5-yl)-pyridine-2,6-diamine;
3-(3-(4-pyridin-2-yloxymethyl)-benzyl)-isoxazol-5-yl)-pyridine-2,6-diamine;
3-(3-(4-(6-methyl-pyridin-2-yloxymethyl)-benzyl)-isoxazol-5-yl)-pyridine-2,6-diamine;
3-(3-(4-butoxymethyl-benzyl)-isoxazol-5-yl)-pyridine-2,6-diamine;
3-(3-(4-phenoxy-benzyl)isoxazol-5-yl)-pyridine-2,6-diamine;
3-(3-(4-(4-methyl-pyridin-2-ylmethoxy)-benzyl)-isoxazol-5-yl)-pyridine-2,6-diamine;
3-(3-(6-benzyloxy-pyridin-3-ylmethyl)-isoxazol-5-yl)-pyridine-2,6-diamine;
6-methoxymethyl-3-(3-(4-pyridin-2-ylmethoxy)-benzyl)-isoxazol-5-yl)-pyridin-2-ylamine;
3-(3-(6-phenoxy-pyridin-3-ylmethyl)-isoxazol-5-yl)-pyridine-2,6-diamine;
3-(3-(4-(5-fluoro-pyridin-2-ylmethoxy)-benzyl)-isoxazol-5-yl)-pyridin-2-ylamine;
3-(3-(4-(4-methyl-pyridin-2-yloxymethyl)-benzyl)-isoxazol-5-yl)-pyridin-2-ylamine;
3-(3-(4-(6-fluoro-pyridin-2-ylmethoxy)-benzyl)-isoxazol-5-yl)-pyridin-2-ylamine;
3-(3-(4-(4-chloro-pyridin-2-ylmethoxy)-benzyl)-isoxazol-5-yl)-pyridin-2-ylamine;
3-(3-(4-(6-chloro-pyridin-2-ylmethoxy)-benzyl)-isoxazol-5-yl)-pyridin-2-ylamine;
3-(3-(6-phenoxymethyl-pyridin-3-ylmethyl)-isoxazol-5-yl)-pyridin-2-ylamine;
3-(3-(4-(6-fluoro-pyridin-2-yloxymethyl)-benzyl)-isoxazol-5-yl)-pyridin-2-ylamine;
3-(3-(6-(4-fluoro-benzyloxy)-pyridin-3-ylmethyl)-isoxazol-5-yl)-pyridin-2-ylamine;
3-(3-(4-(5-chloro-furan-2-ylmethyl)-benzyl)-isoxazol-5-yl)-pyridin-2-ylamine;
3-(3-(4-phenylaminomethyl-benzyl)-isoxazol-5-yl)-pyridin-2-ylamine;
3-(3-(4-(4-methyl-pyridin-2-yloxymethyl)-benzyl)-isoxazol-5-yl)-pyridine-2,6-diamine;
3-(3-(4-(6-fluoro-pyridin-2-ylmethoxy)-benzyl)-isoxazol-5-yl)-pyridine-2,6-diamine;
3-(3-(4-(5-methyl-furan-2-ylmethyl)-benzyl)-isoxazol-5-yl)-pyridine-2,6-diamine;
3-(3-(4-(4-chloro-pyridin-2-ylmethoxy)-benzyl)-isoxazol-5-yl)-pyridine-2,6-diamine;
3-(3-(4-(6-chloro-pyridin-2-ylmethoxy)-benzyl)-isoxazol-5-yl)-pyridine-2,6-diamine;
3-(3-(6-phenoxymethyl-pyridin-3-ylmethyl)-isoxazol-5-yl)-pyridine-2,6-diamine;
3-(3-(4-(5-fluoro-pyridin-2-ylmethoxy)-benzyl)-isoxazol-5-yl)-pyridine-2,6-diamine;
3-(3-(4-(6-fluoro-pyridin-2-yloxymethyl)-benzyl)-isoxazol-5-yl)-pyridine-2,6-diamine;
3-(3-(1-benzyl-1H-pyrrol-3-ylmethyl)-isoxazol-5-yl)-pyridine-2,6-diamine;
3-(3-(6-(4-fluoro-benzyloxy)-pyridin-3-ylmethyl)-isoxazol-5-yl)-pyridine-2,6-diamine;
3-(3-(4-(5-chloro-furan-2-ylmethyl)-benzyl)-isoxazol-5-yl)-pyridine-2,6-diamine;
3-(3-(6-(3-fluoro-phenoxy)-pyridin-3-ylmethyl)-isoxazol-5-yl)-pyridine-2,6-diamine;
3-(3-(4-phenylaminomethyl-benzyl)-isoxazol-5-yl)-pyridine-2,6-diamine;
3-(3-(6-(4-fluoro-phenoxy)-pyridin-3-ylmethyl)-isoxazol-5-yl)-pyridine-2,6-diamine;
3-(3-(4-(thiazol-2-ylmethoxy)-benzyl)-isoxazol-5-yl)-pyridine-2,6-diamine;
3-(3-(5-(4-fluoro-phenoxy-thiophen-2-ylmethyl)-isoxazol-5-yl)-pyridine-2,6-diamine;
6-methoxymethyl-3-(3-(4-pyridin-2-yl methoxy)-benzyl)-isoxazol-5-yl)-pyridin-2-ylamine;
6-methyl-3-(3-(4-pyridin-2-yloxymethyl)-benzyl)-isoxazol-5-yl)-pyridin-2-ylamine;
5-(3-(4-(pyridin-2-yloxymethyl)-benzyl)-isoxazol-5-yl)-pyridin-2-ylamine; and
3-(3-(4-pyridin-2-yloxymethyl)-benzyl)-isoxazol-5-yl)-pyridine.

The compound represented by formula (III) and used as a starting substance in the manufacturing method according to the present invention

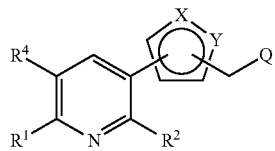
(III)

can be manufactured by a manufacturing method that comprises subjecting a compound represented by the following formula (VI)

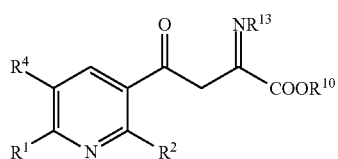
(VI)

to a cyclization reaction; performing a reduction reaction, and then performing halogenation. When $R^2$ represents an amino group having a protective group, the compound represented by formula (III) can also be manufactured by further performing deprotection of the protective group after the above-mentioned reduction reaction. The protective group of the amino group in this case is not limited to the following, but examples thereof may include carbamates such as a methoxycarbonyl group, an ethoxycarbonyl group, or a tert-butoxycarbonyl group; and amide groups such as a formyl group, an acetyl group, or a pivaloyl group. A formyl group, an acetyl group, a pivaloyl group, or a tert-butoxycarbonyl group is preferable, and a pivaloyl group is more preferable.

(wherein $R^1$, $R^2$, $R^4$, X, Y, and Q are defined the same as above, $R^{10}$ represents a hydrogen atom or a $C_{1-6}$ alkyl group, and $R^{13}$ represents a hydroxyl group or a $C_{1-6}$ alkyl group.)

The above structural formula for the compound represents a certain isomer for the sake of convenience, but the present invention encompasses all geometric isomers, optical isomers based on asymmetric carbons, stereoisomers, rotamers, tautomers, and other such isomers and isomer mixtures that can occur in the structure of the compound, and is not limited to what is shown in the formulas for the sake of convenience, and may be any of these isomers or a mixture thereof.

$R^{10}$ preferably represents a methyl group or an ethyl group, and $R^{13}$ preferably represents a hydrogen atom. The cyclization reaction of the compound represented by formula (VI), and the subsequent reduction reaction and halogenation reaction will be discussed in more detail for the general manufacturing method discussed below.

When $R^2$ represents an amino group, protection step of the amino group can be further included if necessary. The protective group that protects the amino group preferably represents an acetyl group, a pivaloyl group, or a tert-butoxycarbonyl group, with a pivaloyl group or a tert-butoxycarbonyl group being more preferable.

Q in formula (III) preferably represents a halogen atom or a substituted sulfonyloxy group. When Q represents a halogen atom, then a chlorine atom or bromine atom is preferable, with a chlorine atom being more preferable. When Q represents a substituted sulfonyloxy group, then a para-toluenesulfonyloxy group or a methanesulfonyloxy group is preferable, with a para-toluenesulfonyloxy group being more preferable.

Next will be described an intermediate that is useful in the manufacture of the compound represented by formula (I) above. More specifically, in one aspect of the present invention, there is provided a compound represented by the following formula (VII) or a salt thereof.

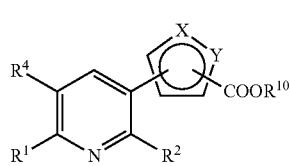
(VII)

In the above formula, $R^1$, $R^2$, $R^4$, X, and Y are defined the same as above, and $R^{10}$ represents a hydrogen atom or a $C_{1-6}$ alkyl group.

The partial structure represented by

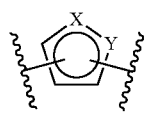
(VIII)

in formula (VII) above preferably represents a structure having an isoxazole skeleton as represented below.

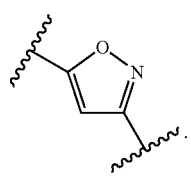
(IX)

Also, $R^{10}$ preferably represents a methyl group or an ethyl group, with an ethyl group being more preferable.

Another intermediate that is useful in the manufacture of the compound represented by formula (I) above will be described. More specifically, in another aspect of the present invention, there is provided a compound represented by the following formula (X) or a salt thereof.

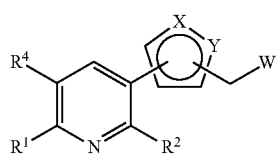
(X)

In the above formula, $R^1$, $R^2$, $R^4$, X, and Y are defined the same as above, and W represents a hydroxyl group, a halogen atom, or a substituted sulfonyloxy group.

The partial structure represented by

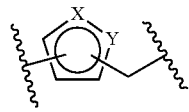

(IV)

in formula (X) above preferably represents a structure having an isoxazole skeleton as represented below.

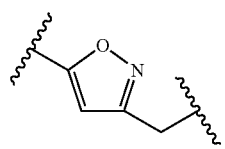

(V)

W preferably represents a hydroxyl group, a chlorine atom, a bromine atom, or a para-toluenesulfonyloxy group, with a hydroxyl group or a chlorine atom being more preferable.

Yet another intermediate that is useful in the manufacture of the compound represented by formula (I) above will be described. More specifically, in yet another aspect of the present invention, there is provided a compound represented by the following formula (XI) or a salt thereof.

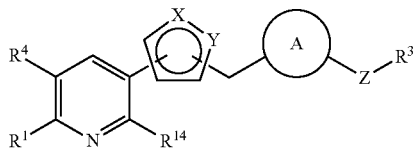

(XI)

In the above formula, $R^1$, $R^3$, $R^4$, X, Y, Z, and the ring A are defined the same as above, and $R^{14}$ represents an amino group protected with a protective group.

When Z represents a single bond, or when $R^3$ represents a hydrogen atom, then $R^1$ and $R^4$ cannot both be a hydrogen atom at the same time.

The partial structure represented by

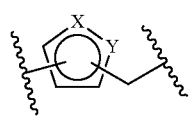

(IV)

in formula (XI) above preferably represents a structure having an isoxazole skeleton as represented below.

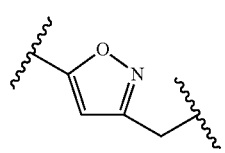

(V)

Examples of the protective group that protects the amino group in $R^{14}$ may include carbamates such as a methoxycarbonyl group, an ethoxycarbonyl group, or a tert-butoxycarbonyl group; and amide groups such as a formyl group, an acetyl group, or a pivaloyl group. When $R^{14}$ represents an amino group protected with a protective group, then one of the hydrogens of the amino group may be protected with a protective group, or two of the hydrogens of the amino group may be protected with a protective group, with a pivaloyl group or a tert-butoxycarbonyl group being preferable, and a tert-butoxycarbonyl group being more preferable.

Still another intermediate that is useful in the manufacture of the compound represented by formula (I) above will be described. More specifically, in yet another aspect of the present invention, there is provided a compound represented by the following formula (XII) or a salt thereof.

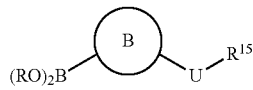

(XII)

In the above formula, the ring B represents a halogen atom or a benzene ring that may have one or two $C_{1-6}$ alkyl groups;
U represents —CH$_2$O—;
R represents a hydrogen atom or a $C_{1-6}$ alkyl group, and when the two R groups represents both $C_{1-6}$ alkyl groups, they may together form a ring; and
$R^{15}$ represents a hydrogen atom or a halogen atom, or a pyridine ring that may have one or two substituents selected from a substituent group α,
[Substituent Group α]
a halogen atom, a cyano group, a $C_{1-6}$ alkyl group, a $C_{1-6}$ alkoxy group, a $C_{1-6}$ alkoxycarbonyl group, a $C_{3-8}$ cycloalkyl group, a $C_{2-6}$ alkenyl group, and a $C_{2-6}$ alkynyl group.

The ring B preferably represents an unsubstituted benzene ring, and R preferably represents a hydrogen atom, or two R groups together form a ring as represented below.

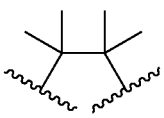

(XIII)

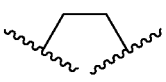

(XIV)

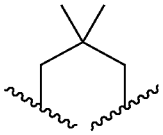

(XV)

(XVI)

$R^{15}$ preferably represents an unsubstituted pyridine ring.

Examples of the term "salt" used in the present specification include a salt with an inorganic acid, a salt with an organic acid, a salt with an inorganic base, a salt with an organic base, a salt with an acidic or basic amino acid or the like. Among these salts, it is preferable that a salt used herein be a pharmaceutically acceptable.

Preferable examples of the salt with the inorganic acid include salts with hydrochloric acid, hydrobromic acid, sulfuric acid, nitric acid, phosphoric acid or the like. Preferable examples of the salt with the organic acid include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid or the like.

Preferable examples of the salt with the acidic amino acid include salts with aspartic acid, glutamic acid or the like.

Preferable examples of the salt with the basic amino acid include salts with arginine, lysine, ornithine or the like.

General Manufacturing Method

The method for manufacturing the compound (14) represented by the above formula (1) and used in the present invention will now be described. The abbreviations used below are defined as follows.

Boc: Cert-butoxycarbonyl
Piv: pivaloyl
Ac: acetyl

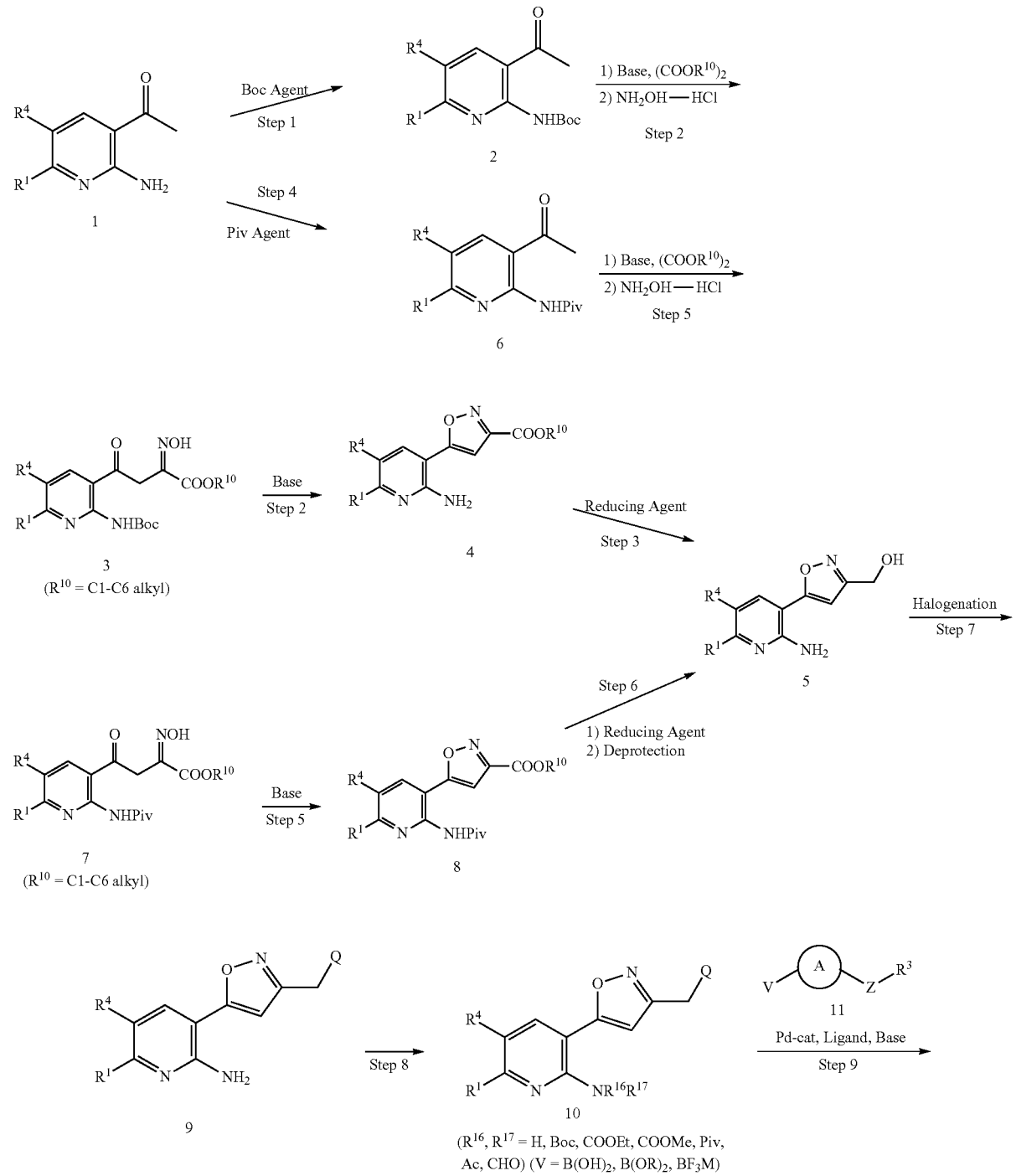

Manufacturing Scheme 1

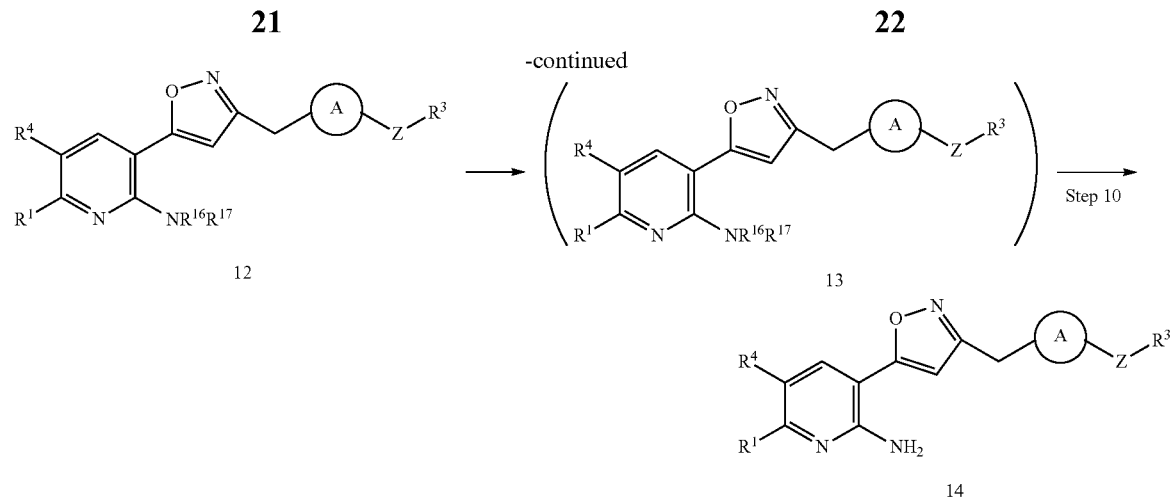

Note that the compound represented by formula (1) is referred to as compound (1), and the compounds represented by the other formulas are referred to similarly. Compound (1) which is a commercially available product can be used as it is, or it can be manufactured by the known method from the commercially available product.

Step 1

This is a step of obtaining compound (2) by reacting compound 1 and a Boc agent. There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; and mixtures of these solvents. Di-tert-butyl dicarbonate or the like can be used as the Boc agent used in this reaction. The Boc agent can be used in an amount of from 1 to 100 equivalents, and preferably from 1 to 10 equivalents, based on compound (1). The reaction temperature is from room temperature to the reflux temperature, and the reaction time is from 1 to 24 hours.

Step 2

This is a step of obtaining compound (4) in the presence of a base via compound (3), by reacting compound (2) obtained in step 1 with an oxalic diester in the presence of a base, and then adding hydroxylamine hydrochloride to the resulting reaction solution. There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl In the above scheme, $R^1$, $R^3$, $R^4$, the ring A, Z, $R^{10}$, and R are defined the same as above.

ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; and mixtures of these solvents. The oxalic diester used in the present invention can be dimethyl oxalate, diethyl oxalate, or the like. The oxalic diester can be used in an amount of from 1 to 100 equivalents, and preferably 1 to 10 equivalents, based on compound (2). The base used in this reaction can be sodium carbonate, triethylamine, or the like. The base can be used in an amount of from 1 to 100 equivalents, and preferably 1 to 10 equivalents, based on compound (2). The hydroxylamine hydrochloride is used in an amount of from 1 to 100 equivalents, and preferably 1 to 10 equivalents, based on compound (2). The reaction temperature is from room temperature to the reflux temperature, and the reaction time is from 1 to 24 hours.

Step 3

This is a step of obtaining compound (5) by reducing compound (4). There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; water; and mixtures of these solvents. The reducing agent used in this reaction can be aluminum lithium hydride, aluminum lithium hydride-aluminum chloride (the aluminum chloride is used in an amount of 1 to 1.5 equivalents based on the aluminum lithium hydride), lithium borohydride, sodium borohydride, or the like. The reducing agent can be used in an amount of from 1 to 100 equivalents, and preferably 1 to 10 equivalents, based on compound (4). The reaction temperature is from 0° C. to the reflux temperature, and the reaction time is from 10 minutes to 48 hours.

Step 4

This is a step of obtaining compound (6) by reacting compound (1) with a Piv agent. There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; and mixtures of these solvents. The Piv agent used in this reaction can be pivaloyl chloride or the like, and this Piv agent is used in an amount of from 1 to 100 equivalents, and preferably 1 to 10 equivalents, based on compound (1). The reaction temperature is from room temperature to the reflux temperature, and the reaction time is from 1 to 24 hours.

Step 5

In this step, compound (6) obtained in step 4 is reacted with an oxalic diester in the presence of a base, and then hydroxylamine hydrochloride is added to the resulting reaction solution to obtain compound (8) in the presence of a base via compound (7). There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; and mixtures of these solvents. The oxalic diester used in the present invention can be dimethyl oxalate, diethyl oxalate, or the like. The oxalic diester can be used in an amount of from 1 to 100 equivalents, and preferably 1 to 10 equivalents, based on compound (6). The base used in this reaction can be sodium carbonate, triethylamine, or the like. The base can be used in an amount of from 1 to 100 equivalents, and preferably 1 to 10 equivalents, based on compound (6). The hydroxylamine hydrochloride is used in an amount of from 1 to 100 equivalents, and preferably 1 to 10 equivalents, based on compound (6). The reaction temperature is from room temperature to the reflux temperature, and the reaction time is from 1 to 24 hours.

Step 6

This is a step of obtaining compound (5) by reducing compound (8). There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate;

water; and mixtures of these solvents. The reducing agent used in this reaction can be aluminum lithium hydride, aluminum lithium hydride-aluminum chloride (the aluminum chloride is used in an amount of 1 to 1.5 equivalents based on the aluminum lithium hydride), lithium borohydride, sodium borohydride, or the like. The reducing agent can be used in an amount of from 1 to 100 equivalents, and preferably 1 to 10 equivalents, based on compound (8). The reaction temperature is from −20° C. to the reflux temperature, and the reaction time is from 10 minutes to 48 hours. In this step, the protective group of the amino group can also be removed after the reduction reaction. There are no particular restrictions on the solvent used in this reaction, as long as it will dissolve the starting material to a certain extent and will not impede the reaction, but examples thereof may include ether-based solvents such as tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; water; and mixtures of these solvents. There are no particular restrictions on the acid used in this reaction, as long as it can promote the reaction, but examples thereof may include mineral acids such as hydrochloric acid, or sulfuric acid; and organic acids such as formic acid, acetic acid, or trifluoroacetic acid. The use of hydrochloric acid, sulfuric acid, formic acid, or trifluoroacetic acid is preferable. There are no particular restrictions on the base used, as long as it can promote the reaction, but examples thereof may include inorganic bases such as sodium hydroxide, or potassium hydroxide.

These reagents can be used in an amount of 0.1 to 100 equivalents, and preferably 1 to 50 equivalents, based on compound (8). The reaction temperature is from −20° C. to the reflux temperature, and the reaction time is from 10 minutes to 48 hours.

Step 7

This is a step of obtaining compound (9) by reacting compound (5) with thionyl chloride. There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; and mixtures of these solvents. The thionyl chloride can be used in an amount of from 1 to 100 equivalents, and preferably 1 to 10 equivalents, based on compound (5). The reaction temperature is from −20° C. to the reflux temperature, and the reaction time is from 10 minutes to 48 hours.

Step 8

This is a step of obtaining compound (10) by reacting compound (9) in the presence of an amino group protecting agent. There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; and mixtures of these solvents. The protecting agent used in this reaction can be acetyl chloride, pivaloyl chloride, di-tert-butyl dicarbonate, or the like. The amino protecting agent can be used in an amount of from 1 to 100 equivalents, and preferably 1 to 10 equivalents, based on compound (9). The reaction temperature is from −20° C. to the reflux temperature, and the reaction time is from 10 minutes to 48 hours.

Step 9

This is a step of obtaining compound (12) by reacting compound (10) with compound (11), which is a {4-[(pyridin-2-yloxy)methyl]phenyl}boronic acid derivative, in an inert solvent and in the presence of a base and a palladium(0) catalyst. There are no particular restrictions on the solvent used in this reaction, as long as it will dissolve the starting material to a certain extent and will not impede the reaction, but examples thereof may include amide-based solvents such as formamide, dimethylformamide, dimethylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; dimethyl sulfoxide, sulfolane, and other such sulfoxide-based solvents; ester-based solvents such as methyl acetate, ethyl acetate, propyl acetate, or diethyl carbonate; water; and mixtures of these solvents. There are no particular restrictions on compound (11) used in this reaction, as long as the targeted compound can be obtained and no inseparable by-products are produced, but V in the formula represents —B(OH)$_2$, —B(OR)$_2$, or —BF$_3$M (wherein M represents sodium or potassium). For example, compound (11) is preferably {4-[(pyridin-2-yloxy)methyl]phenyl}boronic acid, 2-{[4-(5,5-dimethyl-1,3,2-dioxaborinan-2-yl)benzyl]oxy}pyridine, or the like. 2-{[4-(5,5-Dimethyl-1,3,2-dioxaborinan-2-yl)benzyl]oxy}pyridine is more preferable.

This compound (11) can be used in an amount of from 0.5 to 10 equivalents, and preferably 0.5 to 3 equivalents, based on compound (10). There are no particular restrictions on the palladium catalyst used in this reaction, as long as the targeted compound can be obtained and no inseparable by-products are produced, but it can be tetrakis(triphenylphosphine) palladium, tris(dibenzylideneacetone) dipalladium, bis(dibenzylideneacetone) palladium, bis(tri-t-butylphosphine) palladium, palladium black, or the like, or it can be a palladium(0) catalyst that is produced in the reaction system by combining the various ligands listed below and the various palladium complexes that become a palladium(0) precursor listed below.

Specifically, there are no particular restrictions on the various palladium complexes that become a palladium(0) precursor, as long as the targeted compound can be obtained and no inseparable by-products are produced, but specific examples thereof may include palladium acetate, 1,1'-bis(diphenylphosphino)ferrocene chloropalladium, dichlorobis(tri-o-tolylphosphine) palladium, and dichlorobis(triscyclohexylphosphine) palladium. There are no particular restrictions on the ligand, as long as the targeted compound can be obtained and no inseparable by-products are produced, but specific examples thereof may include 2,2'-bis(diphenylphosphino)-1,1'-binaphthyl (BINAP), 9,9-dimethyl-4,5-bis(diphenylphosphino)xanthene (Xantphos), tri-t-butylphosphine, tri (4-methyl phenyl)phosphine, tri-2-furylphosphine, 2-(di-t-butylphosphino)biphenyl, 2-(dicyclohexylphosphino) biphenyl, tricyclohexylphosphine, 2-dicycloheyxiphosphino-2'-(N,N-dimethylamino)biphenyl, 1,1'-bis(diphenylphosphino)ferrocene, (oxidine-2,1-phenylene)bis(diphenylphosphine), di-t-butyl phosphonium tetrafluoroborate, and 1,3-bis(2,4,6-trimethylphenyl)imidazol-2-ylidene.

The above-mentioned palladium(0) catalyst can be used in an amount of 0.01 to 5 molar equivalents, and preferably 0.01 to 0.1 molar equivalent, based on mole of compound (10).

Also, there are no particular restrictions on the base that is used in this reaction, as long as the targeted compound can be obtained and no inseparable by-products are produced, but specific examples thereof may include inorganic bases such as tripotassium phosphate, trisodium phosphate, cesium carbonate, potassium carbonate, sodium carbonate, cesium hydrogencarbonate, potassium hydrogencarbonate, sodium hydrogencarbonate, sodium acetate, barium hydroxide, potassium hydroxide, potassium fluoride, or cesium fluoride; metal alkoxides such as sodium ethoxide, or sodium t-butoxide; acetates of alkali metals such as sodium acetate or potassium acetate; and organic bases such as triethylamine, and potassium carbonate, sodium carbonate are favorable. The base can be used in an amount of 0.5 to 100 equivalents, and preferably 0.5 to 3 equivalents, based on compound (10). The reaction temperature is from 0° C. to the reflux temperature, and the reaction time is from 10 minutes to 48 hours.

Step 10

This is a step of obtaining compound (14) via compound (13) by removing the protective group from the amino group of compound (12). There are no particular restrictions on the solvent used in this reaction, as long as it will dissolve the starting material to a certain extent and will not impede the reaction, but examples thereof may include amide-based solvents such as formamide, dimethylformamide, di methylacetamide, hexamethyl phosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; water; and mixtures of these solvents. Any known deprotecting reaction can be used as the method for removing the protective group of the amino group used in this reaction, but when the protective group is a t-butoxycarbonyl group, for example, the method described in *Synthesis*, pp. 66-68, 1999, etc., can be used, and when the protective group is an acetyl group, the method described in *J. Org. Chem.*, pp. 4593, 1978, etc., can be used to remove the protection of amino group.

There are no particular restrictions on the acid used, as long as it can promote the reaction, but examples thereof may include mineral acids such as hydrochloric acid, or sulfuric acid; and organic acids such as formic acid, acetic acid, trifluoroacetic acid. The use of hydrochloric acid, sulfuric acid, formic acid, or trifluoroacetic acid is preferable.

There are no particular restrictions on the base used, as long as it can promote the reaction, but examples thereof may include inorganic bases such as sodium hydroxide, or potassium hydroxide; and organic bases such as hydrazine, alkylamines.

These reagents can be used in an amount of 0.1 to 100 equivalents, and preferably 1 to 50 equivalents based on compound (11). The reaction temperature is from −20° C. to the reflux temperature, and the reaction time is from 10 minutes to 48 hours.

Step 11

This is a step of obtaining compound (10) by reacting compound (15) with p-toluenesulfonyl chloride or another such sulfonyl chloride. There are no particular restrictions on the solvent used in this reaction, as long as it will dissolve the starting material to a certain extent and will not impede the reaction, but examples thereof may include amide-based solvents such as formamide, dimethylformamide, di methylacetamide, hexamethylphosphoric triamide, 1,3-dimethyl-2-imidazolidinone, or N-methylpyrrolidone; aromatic hydrocarbon-based solvents such as toluene, benzene, xylene, or mesitylene; ether-based solvents such as diethyl ether, diisopropyl ether, tetrahydrofuran, dioxane, dimethoxyethane, or diethylene glycol dimethyl ether; alcohol-based solvents such as methanol, ethanol, n-propanol, isopropanol, n-butanol, isobutanol, t-butanol, isoamyl alcohol, diethylene glycol, glycerol, octanol, cyclohexanol, or methyl cellosolve; nitrile-based solvents such as acetonitrile, or isobutyronitrile; sulfoxide-based solvents such as dimethyl sulfoxide, or sulfolane; ester-based solvents such as methyl acetate, ethyl acetate, propyl acetate, or diethyl carbonate; and mixtures of these solvents. The p-toluenesulfonyl chloride can be used in an amount of from 1 to 100 equivalents, and preferably 1 to 10 equivalents, based on compound (15). The reaction temperature is from −20° C. to the reflux temperature, and the reaction time is from 10 minutes to 48 hours.

Manufacturing Scheme 3

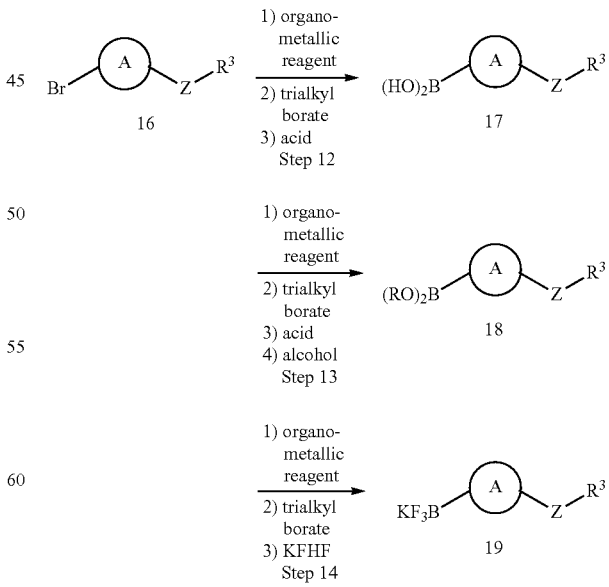

In the above scheme, $R^3$, the ring A, Z, and R are defined the same as above.

Compounds (17), (18), and (19) can be manufactured from compound (16) by the known method (such as that in *Tetrahedron*, Vol. 45, No. 7, pp. 1859-1885, 1989).

Step 12

This is a step of manufacturing compound (17) by reacting a boronic ester with an anionized compound produced by a reaction between compound (16) and an organometallic reagent, and then adding an acid to neutralize the reaction mixture. This reaction can be carried out under an atmosphere or a gas flow of nitrogen, argon, or another such inert gas. There are no particular restrictions on the solvent used in this reaction, as long as it will dissolve the starting material to a certain extent and will not impede the reaction, but examples thereof may include ether-based solvents such as tetrahydrofuran, 1,2-dimethoxyethane, methyl-tert-butyl ether, cyclopentyl methyl ether, diethyl ether, diisopropyl ether, dibutyl ether, or dicyclopentyl ether; aromatic hydrocarbon-based solvents such as benzene, or toluene; aliphatic hydrocarbon-based solvents such as heptane, or hexane; and mixtures of these solvents. The use of tetrahydrofuran is preferable. The above-mentioned "organometallic reagent" refers, for example, to a Grignard's reagent, n-butyl lithium, s-butyl lithium, or the like. The use of n-butyl lithium is preferable. As to the reaction temperature, 30 to 120° C. is preferable for preparing a Grignard's reagent, −80 to −50° C. is preferable for lithiation, −80 to 30° C. is preferable for boronic esterification, and −20 to 30° C. is preferable for hydrolysis. The above-mentioned boronic ester refers, for example, to trimethyl borate or triisopropyl borate. The use of triisopropyl borate is preferable. The above-mentioned acid refers, for example, to an ammonium chloride aqueous solution, methanesulfonic acid, p-toluenesulfonic acid, a hydrochloric acid-ethyl acetate solution, a hydrochloric acid-methanol solution, or hydrochloric acid. An ammonium chloride aqueous solution or hydrochloric acid is preferable.

Step 13

This is a step of manufacturing compound (18) by reacting a boronic ester with an anionized compound produced by a reaction between compound (16) and an organometallic reagent, and then adding an acid to neutralize the reaction mixture, and finally reacting with an alcohol or with pinacol, neopentyl glycol, or another such diol. This reaction can also be carried by adding an organometallic reagent to a mixture of compound (16) and a boronic ester, and reacting with a boronic ester simultaneously with the production of an anion of compound (16). This reaction can be carried out under an atmosphere or a gas flow of nitrogen, argon, or another such inert gas. There are no particular restrictions on the solvent used in this reaction, as long as it will dissolve the starting material to a certain extent and will not impede the reaction, but examples thereof may include ether-based solvents such as tetrahydrofuran, 1,2-dimethoxyethane, methyl-tert-butyl ether, cyclopentyl methyl ether, diethyl ether, diisopropyl ether, dibutyl ether, or dicyclopentyl ether; aromatic hydrocarbon-based solvents such as benzene, or toluene; aliphatic hydrocarbon-based solvents such as heptane, or hexane; and mixtures of these solvents. The use of tetrahydrofuran is preferable. The above-mentioned boronic ester refers, for example, to trimethyl borate or trisopropyl borate. The use of trisopropyl borate is preferable. The above-mentioned "organometallic reagent" refers, for example, to a Grignard's reagent, n-butyl lithium, s-butyl lithium, or the like. The use of n-butyl lithium is preferable. As to the reaction temperature, 30 to 120° C. is preferable for preparing a Grignard's reagent, −80 to −50° C. is preferable for lithiation, −80 to 30° C. is preferable for boronic esterification, and −20 to 30° C. is preferable for hydrolysis. The above-mentioned boronic ester refers, for example, to trimethyl borate or triisopropyl borate. The use of triisopropyl borate is preferable. The above-mentioned acid refers, for example, to an ammonium chloride aqueous solution, methanesulfonic acid, p-toluenesulfonic acid, a hydrochloric acid-ethyl acetate solution, a hydrochloric acid-methanol solution, or hydrochloric acid. An ammonium chloride aqueous solution or hydrochloric acid is preferable.

Step 14

This is a step of manufacturing compound (19) by reacting a boronic ester with an anionized compound produced by a reaction between an organometallic reagent and compound (16), and then reacting with a hydrogen fluoride salt (potassium hydrogen fluoride, sodium hydrogen fluoride, etc.). This reaction can be carried out under an atmosphere or a gas flow of nitrogen, argon, or another such inert gas. There are no particular restrictions on the solvent used in this reaction, as long as it will dissolve the starting material to a certain extent and will not impede the reaction, but examples thereof may include ether-based solvents such as tetrahydrofuran, 1,2-dimethoxyethane, methyl-tert-butyl ether, cyclopentyl methyl ether, diethyl ether, diisopropyl ether, dibutyl ether, or dicyclopentyl ether; aromatic hydrocarbon-based solvents such as benzene, or toluene; aliphatic hydrocarbon-based solvents such as heptane, or hexane; and mixtures of these solvents. The use of tetrahydrofuran is preferable. The above-mentioned boronic ester refers, for example, to trimethyl borate or triisopropyl borate. The use of triisopropyl borate is preferable. The above-mentioned "organometallic reagent" refers, for example, to a Grignard's reagent, n-butyl lithium, s-butyl lithium, or the like. The use of n-butyl lithium is preferable. As to the reaction temperature, 30 to 120° C. is preferable for preparing a Grignard's reagent, −80 to −50° C. is preferable for lithiation, −80 to 30° C. is preferable for boronic esterification, and −20 to 30° C. is preferable for hydrolysis. The above-mentioned boronic ester refers, for example, to trimethyl borate or triisopropyl borate. The use of triisopropyl borate is preferable.

EXAMPLES

The present invention will now be described in specific terms on the basis of examples, but the present invention is not limited to or by these examples. A person skilled in the art will be able to work the present invention by adding various modifications to the examples given below, and such modifications are encompassed by the claims of this application. In the following examples, compounds synthesized according to the above-mentioned schemes will use the numbers given for those schemes, and will be called "compound 1," etc.

Manufacturing Example 1

Synthesis of tert-butyl(3-acetylpyridin-2-yl)carbamate

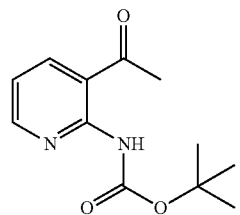 [SMILES: CC(=O)c1cccnc1NC(=O)OC(C)(C)C]

A mixture of 1-(2-aminopyridin-3-yl)ethanone (50 g, 368 mmol), di-tert-butyldicarbonate (120 g, 552 mmol) and tert-butanol (200 mL) was stirred at 90° C. for three hours under a nitrogen atmosphere. After cooling, the solvent was evaporated under a reduced pressure, n-heptane (500 mL) was added to the residue and the precipitated solid was filtered, so as to obtain the title compound (77 g) as a yellow solid.

$^1$H-NMR Spectrum (CDCl$_3$) δ (ppm):1.54(9H,s), 2.64(3H, s), 7.03(1H,dd,J=4.8,8.0 Hz), 8.16(1H,dd,J=2.0,8.0 Hz), 8.63 (1H,dd,J=2.0,4.8 Hz), 10.82(1H,brs).

Example 1

Synthesis of ethyl 5-(2-aminopyridin-3-yl)isoxazol-3-carboxylate

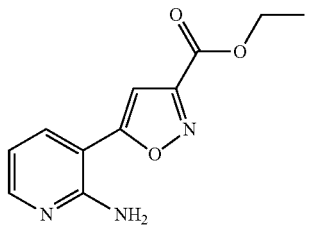 [SMILES: CCOC(=O)c1cc(-c2cccnc2N)on1]

To a solution of tert-butyl (3-acetylpyridin-2-yl)carbamate (600 mg, 2.29 mmol) and diethyl oxalate (669 mg, 4.58 mmol) in toluene (5.0 mL) was added potassium tert-butoxide (514 mg, 4.58 mmol) at room temperature under a nitrogen atmosphere, which was stirred for two hours. After addition of toluene (5.0 mL) and stirring for one hour, potassium tert-butoxide (257 mg, 2.29 mmol) was added thereto and the solution was stirred for two hours. To the reaction mixture were added hydroxylamine hydrochloride (477 mg, 6.87 mmol) and ethanol (10 mL), which was stirred for one hour, water (1.0 mL) was added thereto and the solution was stirred overnight at room temperature. Water (30 mL) was added thereto and the solution was extracted with ethyl acetate. After the organic layer was washed with saturated sodium chloride water and dried over anhydrous magnesium sulfate, the solution was concentrated. The concentrated residue was dissolved in N,N-dimethyl formamide (5 mL), triethylamine (192 mg) was added thereto, and the solution was stirred at 80° C. for six hours. After cooling, water was added thereto, and the solution was extracted with ethyl acetate. After the organic layer was washed with saturated sodium chloride water and dried over anhydrous magnesium sulfate, the solvent was evaporated under a reduced pressure, so as to obtain the title compound (443 mg) as a white solid.

$^1$H-NMR Spectrum (CDCl$_3$) δ (ppm):1.45(3H,t,J=7.2 Hz), 4.49(2H,q,J=7.2 Hz), 5.40(2H,brs), 6.79(1H,dd,J=5.2,7.6 Hz), 6.91(1H,s), 7.81(1H,dd,J=2.0,7.6 Hz), 8.21(1H,dd, J=2.0,5.2 Hz).

Example 2

Synthesis of [5-(2-aminopyridin-3-yl)isoxazol-3-yl]methanol

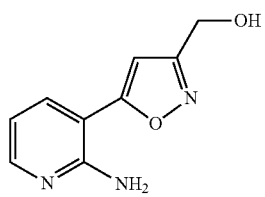 [SMILES: Nc1ncccc1-c1cc(CO)no1]

To a suspension of ethyl 5-(2-aminopyridin-3-yl)isoxazol-3-carboxylate (381 mg, 1.63 mmol) in tetrahydrofuran (3.8 mL) and ethanol (3.8 mL) was added sodium borohydride (201 mg, 4.89 mmol) at 0° C. under a nitrogen atmosphere, which was stirred at 0° C. for one hour and at 20° C. for 21 hours. Under an ice water bath cooling, to the reaction mixture was added 2N hydrochloric acid (2.46 mL, 4.89 mmol) dropwise, which was stirred at 0° C. for 10 minutes and at room temperature for 30 minutes. Under the ice water bath cooling, after an aqueous solution of 5% sodium bicarbonate was added dropwise to adjust basic, the solution was extracted with ethyl acetate. After the organic layer was dried over anhydrous magnesium sulfate, the solvent was evaporated under a reduced pressure. The residue was suspended in tetrahydrofuran (1.4 mL), to the reaction mixture was added sodium borohydride (67 mg, 1.63 mmol) at 0° C., which was washed thereto down with methanol (1.4 mL). After stirring at room temperature for one hour, the solution was stirred at 60° C. for five hours. Under an ice water bath cooling, to the reaction mixture was added 1N hydrochloric acid (1.63 mL, 1.63 mmol) dropwise, which was stirred at 0° C. for 10 minutes and at room temperature for 30 minutes. Under the ice water bath cooling, after adding 1N aqueous sodium hydroxide dropwise to adjust basic, the solution was extracted with ethyl acetate. After the organic layer was dried over anhydrous magnesium sulfate, the solvent was evaporated under a reduced pressure, so as to obtain the title compound (258 mg) as a pale yellow solid.

$^1$H-NMR Spectrum (DMSO-d$_6$) δ (ppm):4.56(2H,d,J=5.6 Hz), 5.54(1H,t,J=5.6 Hz), 6.27(2H,brs), 6.72(1H,dd,J=4.8, 7.6 Hz), 6.90(1H,s), 7.90(1H,dd,J=2.0,7.6 Hz), 8.10(1H,dd, J=2.0,4.8 Hz).

Manufacturing Examples 2 to 4 and Examples 3 to 5 are other synthesis methods to Examples 1 and 2.

Manufacturing Example 2

Synthesis of N-(3-acetylpyridin-2-yl)-2,2-dimethylpropanamide

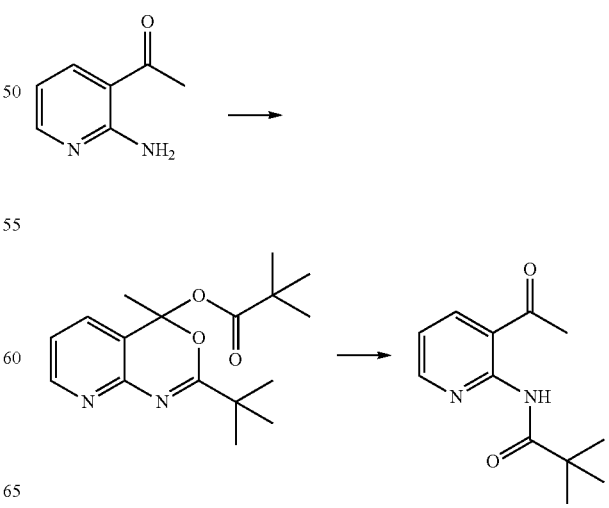

To a mixture of 1-(2-aminopyridin-3-yl)ethanone (272 mg, 2 mmol), 4-dimethylaminopyridine (24 mg, 0.2 mmol), triethylamine (0.64 mL, 4.6 mmol) and toluene (2 mL) was added pivaloyl chloride (0.52 mL, 4.2 mmol) dropwise at room temperature, which was stirred at room temperature for one hour and at 60° C. for five hours. After formation of 2-tert-butyl-4-methyl-4H-pyrido[2,3-d][1,3]oxazin-4-yl pivalate* was confirmed, to the reaction mixture were added water (2 mL) and 5N hydrochloric acid (0.8 mL), which was stirred at room temperature for 30 minutes. After the reaction mixture was separated, to the aqueous layer was added 5N aqueous sodium hydroxide (1 mL) and extracted with toluene. The solvent was evaporated under a reduced pressure and the precipitated solid was filtered, so as to obtain the title compound (415 mg).

*2-tert-butyl-4-methyl-4H-pyrido[2,3-d][1,3]oxazin-4-yl pivalate $^1$H-NMR Spectrum (CDCl$_3$) δ (ppm):1.33(9H,s), 2.64(3H, s), 7.10(1H,dd,J=4.8,8.0 Hz), 8.17(1H,dd,J=2.0,7.6 Hz), 8.64 (1H,dd,J=2.0,4.8 Hz).

$^1$H-NMR Spectrum (CDCl$_3$) δ (ppm):1.09 (9H,s), 1.32 (9H,s), 2.05 (3H,s), 7.14 (1H,dd,J=4.8,7.6 Hz), 7.71 (1H,dd,J=2.0,7.6 Hz), 8.51 (1H,dd,J=2.0,4.8 Hz).

Manufacturing Examples 3 to 4 are other synthesis methods to Manufacturing Example 2.

Manufacturing Example 3

Synthesis of 2-tert-butyl-4H-pyrido[2,3-d][1,3]oxazin-4-one

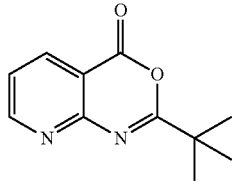

To a mixture of 2-aminonicotinic acid (13.8 g, 100 mmol), 4-dimethylaminopyridine (1.2 g, 10 mmol), triethylamine (55.8 mL, 400 mmol) and N-methylpyrrolidone (140 mL, 42 mmol) was added pivaloyl chloride (24.1 g, 200 mmol) dropwise at 0° C., and after the drop wise addition was finished, which was stirred overnight at room temperature. To the reaction mixture was added water, extracted with toluene, and the organic layer was washed with water and saturated sodium chloride water. After the solution was dried over anhydrous magnesium sulfate and filtered, the solvent was evaporated under a reduced pressure. To the residue was added n-heptane, which was suspended and stirred at 0° C., which was filtered, so as to obtain the title compound (16.6 g).

$^1$H-NMR Spectrum (CDCl$_3$) δ (ppm):1.45(9H,s), 7.48(1H, dd,J=4.8,8.0 Hz), 8.52(1H,dd,J=2.0,7.6 Hz), 8.97(1H,dd, J=2.0,4.8 Hz).

Manufacturing Example 4

Synthesis of N-(3-acetyl pyridin-2-yl)-2,2-dimethylpropanamide

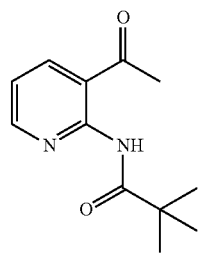 [SMILES: CC(=O)c1cccnc1NC(=O)C(C)(C)C]

To a mixture of 2-tert-butyl-4H-pyrido[2,3-d][1,3]oxazin-4-one (10.2 g, 50 mmol) and tetrahydrofuran (50 mL) was added methyl magnesium bromide (0.97M tetrahydrofuran solution, 100 mL, 97 mmol) dropwise at −78° C., after the dropwise addition was finished, which was stirred at −78° C. for 30 minutes. To the reaction mixture were added a saturated aqueous solution of ammonium chloride and water, which was extracted with ethyl acetate, and the organic layer was washed with an aqueous solution of ammonium chloride. The solvent was evaporated under a reduced pressure and the precipitated solid was filtered, so as to obtain the title compound (9.1 g).

$^1$H-NMR Spectrum (CDCl$_3$) δ (ppm):1.33(9H,s), 2.64(3H, s), 7.10(1H,dd,J=4.8,8.0 Hz), 8.17(1H,dd,J=2.0,7.6 Hz), 8.64 (1H,dd,J=2.0,4.8 Hz).

Example 3

Synthesis of ethyl 5-{2-[(2,2-dimethylpropanoyl)amino]pyridin-3-yl}isoxazol-3-carboxylate

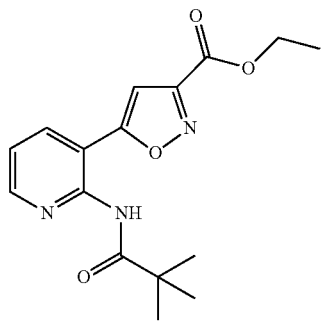 [SMILES: CCOC(=O)c1cc(-c2cccnc2NC(=O)C(C)(C)C)on1]

To a mixture of N-(3-acetyl pyridin-2-yl)-2,2-dimethylpropanamide (8.08 g, 36.7 mmol), diethyl oxalate (10.0 mL, 73.4 mmol) and ethanol (36 mL) was added potassium tert-butoxide (8.23 g, 73.4 mmol) at −25° C., which was stirred at −25° C. for one hour. The reaction mixture was added water (72 mL), which was stirred at room temperature, toluene (36 mL) was added, separated, and the obtained aqueous layer was further washed with toluene (36 mL). To the solution were added 5N hydrochloric acid (14 mL) and hydroxylamine hydrochloride (5.10 g, 73.4 mmol), which was stirred at room temperature for 30 minutes. To the reaction mixture was added 5N aqueous sodium hydroxide (14 mL), which was extracted with toluene, the solvent was evaporated under a reduced pressure. To the obtained residue were added ethanol (35 mL) and triethylamine (5 mL), which was stirred at 80° C. to 85° C. for six hours. To the reaction mixture was added n-heptane (105 mL) and the precipitated solid was filtered, so as to obtain the title compound (6.90 g).

$^1$H-NMR Spectrum (DMSO-d6) δ (ppm):1.19(9H,s), 1.32 (3H,t), 4.37(4H,q), 7.12(1H,s), 7.46(1H,dd,J=4.8,8.0 Hz), 8.25(1H,dd,J=2.0,8.0 Hz), 8.58(1H,dd,J=2.0,4.8 Hz), 10.03 (1H,s).

Example 4

Synthesis of N-{3-[3-(hydroxymethyl)isoxazol-5-yl]pyridin-2-yl}-2,2 dimethylpropanamide

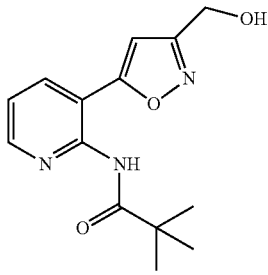 [SMILES: CC(C)(C)C(=O)Nc1ncccc1-c1cc(CO)no1]

To a mixture of ethyl 5-{2-[(2,2-dimethylpropanoyl)amino]pyridin-3-yl}isoxazol-3-carboxylate (111 g, 350 mmol), ethanol (110 mL) and tetrahydrofuran (350 mL) was added sodium borohydride (13.2 g, 350 mmol) at room temperature, which was stirred at room temperature for 6 hours. To the reaction mixture were added water (350 mL) and 5N hydrochloric acid (90 mL), which was stirred at room temperature for 30 minutes, 5N aqueous sodium hydroxide (110 mL) was added thereto, the solution was extracted with a mixture of ethyl acetate and tetrahydrofuran, and the organic layer was washed with water and saturated sodium chloride water. The solvent was evaporated under a reduced pressure, so as to obtain the title compound (83.8 g) as a yellow solid, partially contaminated with [5-(2-aminopyridin-3-yl)isoxazol-3-yl]methanol.

$^1$H-NMR Spectrum (DMSO-$d_6$) δ (ppm):1.20(9H,s), 4.52 (2H,d,J=6.0 Hz), 5.53(1H,t,J=6.0 Hz), 6.70(1H,s), 7.44(1H, dd,J=4.8,8.0 Hz), 8.19(1H,dd,J=5.6,7.6 Hz), 8.53(1H,dd, J=2.0,4.8 Hz), 9.89(1H,brs).

Example 5

Synthesis of [5-(2-aminopyridin-3-yl)isoxazol-3-yl]methanol

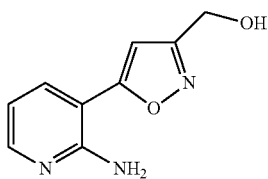

To a mixture of N-{3-[3-(hydroxymethyl)isoxazol-5-yl]pyridin-2-yl}-2,2 dimethylpropanamide (82.8 g) obtained in Example 4 and methanol (350 mL) was added 5N aqueous sodium hydroxide (350 mL) at room temperature, which was stirred at 57 to 60° C. for 14 hours. To the reaction mixture was added acetic acid (100 mL) and the precipitated solid was filtered, so as to obtain the title compound (42.2 g) as a grayish white solid.

$^1$H-NMR Spectrum (DMSO-$d_6$) δ (ppm):4.54(2H,s), 5.57 (1H,brs), 6.25(2H,brs), 6.71(1H,dd,J=4.8,8.0 Hz), 6.90(1H, s), 7.90(1H,dd,J=1.6,7.6 Hz), 8.09(1H,dd,J=1.6,4.8 Hz).

Manufacturing Example 5 and Examples 6 and 7 are other synthesis methods to Manufacturing Examples 2 to 4 and Examples 3 to 5.

Manufacturing Example 5

Synthesis of N-(3-acetylpyridin-2-yl)-2,2-dimethylpropanamide

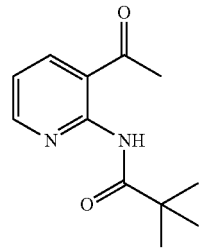 [SMILES: CC(=O)c1cccnc1NC(=O)C(C)(C)C]

After 1-(2-aminopyridin-3-yl)ethanone (40.0 kg, 294 mol) was added to a 1500 L reactor, which was washed thereto down with toluene (approximately 15 kg). Then, after toluene was added until there was 347 kg of toluene in total, pivaloyl chloride (53.1 kg, 1.5M/M) was added thereto. Triethylamine (23.8 kg, 0.8M/M) was added thereto dropwise at an internal temperature of 30° C. or lower and the solution was stirred at an internal temperature of from 20 to 30° C. for one hour or longer. After triethylamine (23.8 kg, 0.8M/M) was again added dropwise at an internal temperature of 30° C. or lower, the solution was stirred at an internal temperature of from 20 to 30° C. for two hours or longer, it was confirmed by HPLC that the reaction had ended.

Under a brine cooling, water (100 L) was added dropwise at an internal temperature of 30° C. or lower, then, 35% hydrochloric acid (49.0 kg, 1.6M/M) was added thereto dropwise at an internal temperature of 30° C. or lower. After the reaction solution was stirred for five minutes, the solution was left standing still for 15 minutes or longer and lower layer (a) was separated into a poly container. After water (100 L) was added thereto and the solution was stirred for five minutes, the solution was left standing still for 15 minutes or longer. After lower layer (c) was separated into a poly container and upper layer (d) was removed, lower layer (a) and lower layer (c) were returned into the 1500 L reactor. Under the brine cooling, ethyl acetate (289 kg) was added thereto, then, after an aqueous solution of 48.7% sodium hydroxide (43.4 kg, 1.8M/M) was added dropwise at an internal temperature of 30° C. or lower and the solution was stirred for five minutes, it was confirmed with a UNIV test paper that a pH of the lower layer was from 8 to 9. After being left standing still for 15 minutes or longer, lower layer (e) and upper layer (f) were each separated and lower layer (e) was returned into the 1500 L reactor. After ethyl acetate (144 kg) was added thereto and the solution was stirred for five minutes, the solution was left standing still for 15 minutes or longer and lower layer (g) and upper layer (h) were each separated. After lower layer (g) was returned into the 1500 L reactor, ethyl acetate (144 kg) was added thereto and the solution was stirred for five minutes, the solution was left standing still for 15 minutes or longer. After removing lower layer (i), upper layer (f) and upper layer (h) were returned into the 1500 L reactor and which was washed thereto down with ethyl acetate (approximately 15 kg).

The organic layer returned into the 1500 L reactor was concentrated under a reduced pressure (50° C. hot water), and concentration was stopped once at the point of time when the concentrate reached approximately 200 L. The concentrate was removed into SUS containers and the inside of the reactor was washed out with toluene (17 kg). Approximately half of the amount of the removed concentrate was placed in a 300 L reactor and washed thereto down with toluene (9 kg). The concentrate was further concentrated under a reduced pressure (50° C. hot water), and when the amount of distillation from the condenser decreased, the remaining concentrate was placed in the 300 L reactor and which was washed thereto down with toluene (9 kg). Concentration under a reduced pressure was restarted (50° C. to 70° C. hot water). At the point of time when there was almost no distillation, water cooling was started and toluene (52 kg) was added thereto at an internal temperature of 50° C. or lower. Concentration under a reduced pressure was restarted (50 to 80° C. hot water). Concentration was stopped at the point of time when distillation was no longer observed at an external temperature of 80° C. and a reduced pressure level of −0.090 MPa or greater, and ethanol (61 kg) was added thereto at an internal temperature of from 20 to 30° C.

Under a nitrogen atmosphere, the ethanol solution inside the can was removed into a SUS container, and the can was washed out with ethanol (13 kg).

After the removed solution was added into the 1500 L reactor, which was washed thereto down with ethanol (13 kg) to obtain an ethanol solution of the title compound (containing 69.4 kg of the target compound; yield: 107.3%).

HPLC conditions: column: YMC-Pack Pro C18 (5 μm, 150×4.6 mml.D., YMC), mobile phase: acetonitrile/water/ammonium acetate=300/700/1 to 900/100/1 (v/v/w).

Example 6

Synthesis of ethyl 5-{2-[(2,2-dimethylpropanoyl)amino]pyridin-3-yl}isoxazol-3-carboxylate

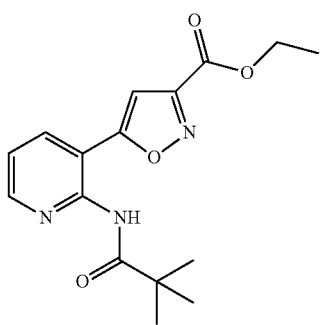 [SMILES: CCOC(=O)c1cc(-c2cccnc2NC(=O)C(C)(C)C)on1]

Under a nitrogen gas stream, diethyl oxalate (64.4 kg, 1.5M/M) was added to the ethanol solution of N-(3-acetyl pyridin-2-yl)-2,2-dimethylpropanamide (294 mol, assuming that the yield of the previous step was 100%) in the 1500 L reactor. Brine circulation was started and a pre-cooled ethanol solution of 22% potassium tert-butoxide (212.5 kg, 1.45M/M) was added dropwise thereto at an internal temperature of 10° C. or lower. After stirring at an internal temperature of from −5 to 10° C. for 30 minutes or longer, it was confirmed by HPLC that the reaction had ended.

Next, hydroxylamine hydrochloride (40.8 kg, 2.0 M/M) was added thereto at an internal temperature of 10° C. or lower, and the solution was stirred at an internal temperature of 10° C. or lower for one hour or longer. Next, prepared and cooled beforehand, hydrous ethanol (ethanol (15.3 kg)/water (5.2 kg)) was added dropwise thereto at an internal temperature of 20° C. or lower while watching for heating, and water (582 L) was added dropwise at an internal temperature of 30° C. or lower. Switching to hot water (28° C.) circulation, ethyl 4-{2-[(2,2-dimethylpropanoyl)amino]pyridin-3-yl}-2-(hydroxyimino)-4-oxobutanoate (approximately 10 g) was added thereto at an internal temperature of from 20 to 30° C. After confirming the precipitation of solid visually, the suspention was stirred overnight at an internal temperature of from 15 to 25° C. After confirming by HPLC that the reaction had ended, and an aqueous solution of 48.7% sodium hydroxide was added dropwise thereto at an internal temperature of from 10 to 25° C. until a pH of the solution was from 6.50 to 7.00 (18.1 kg used). After stirring at an internal temperature of from 10 to 20° C. for three hours or longer, solid-liquid separation was carried out with a centrifuge divided into six times. At each centrifugation, after washing the cake with hydrous ethanol (ethanol (2.4 kg)/water (12 kg)) prepared beforehand, the cake was washed with water until a color of the wash was colorless transparent (approximately 200 L). After centrifugal separation was continued further for 30 minutes or longer, and a wet solid was removed into a poly bag. Next, in a shelf dryer, under 45 to 50° C. hot water circulation, the wet solid was dried under a reduced pressure, so as to obtain a solid (71.52 kg).

Next, the solid obtained above (71.45 kg) was added to the 1500 L reactor and washed thereto down with ethanol (approximately 7 kg). Then, ethanol was added up to 226 kg in total and triethylamine (21.6 kg, 1 M/M) was added thereto. Hot water (75° C.) circulation was started, the solution was stirred at an internal temperature of from 70 to 75° C. for 14 to 16 hours, and it was confirmed by HPLC that the reaction had ended. Next, n-heptane (488.7 kg) was added dropwise thereto at an internal temperature of from 55 to 75° C. Thereafter, ethyl 5-{2-[(2,2-dimethylpropanoyl)amino]pyridin-3-yl}isoxazol-3-carboxylate (approximately 5 g) was added thereto at an internal temperature of from 50 to 53° C., and it was confirmed visually that a solid precipitated at an internal temperature of from 45 to 50° C. Then, after the temperature of hot water was decreased gradually, cooling to an internal temperature of 15° C. or lower, further, by brine or cold water cooling, the solution was stirred overnight at an internal temperature of from 0 to 10° C. Using a filtration apparatus, the suspension was filtered and washed with a mixed solution of n-heptane/ethanol (n-heptane (70 kg)/ethanol (10 kg)), followed by n-heptane (80 kg). After drying was carried out in nitrogen for 15 minutes or longer subsequent, a wet solid was removed to a SUS container. In a shelf dryer under 45 to 50° C. hot water circulation, the wet solid was dried under a reduced pressure, so as to obtain the title compound (54.55 kg; yield: 58.6%).

$^1$H-NMR Spectrum (DMSO-d6) δ (ppm):1.19(9H,s), 1.32(3H,t), 4.37(4H,q), 7.12(1 H,s), 7.46(1H,dd,J=4.8,8.0 Hz), 8.25(1H,dd,J=2.0,8.0 Hz), 8.58(1H,dd,J=2.0,4.8 Hz), 10.03(1H,s).

HPLC conditions: column: YMC-Pack Pro C18 (5 μm, 150×4.6 mml.D., YMC), mobile phase: acetonitrile/water/ammonium acetate=300/700/1 to 900/100/1 (v/v/w).

Example 7

Synthesis of [5-(2-aminopyridin-3-yl)isoxazol-3-yl]methanol

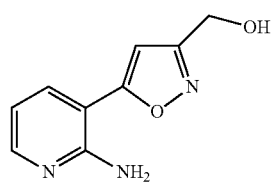 [SMILES: Nc1ncccc1-c1cc(CO)no1]

Under a nitrogen gas stream, ethyl 5-{2-[(2,2-dimethyl-propanoyl)amino]pyridin-3-yl}isoxazol-3-carboxylate (54.5 kg, 172 mol) was added to a 1500 L reactor and washed thereto down with methanol (4.9 kg). Then, methanol was added thereto until there was 108 kg of methanol in total and triethylamine (8.7 kg, 0.5M/M) was added consecutively. After hot water (60° C.) circulation was started, the solution was stirred at an internal temperature of from 50 to 60° C. for two hours or longer, and it was confirmed by HPLC (Condition 1) that the reaction had ended.

Next, water cooling was started and tetrahydrofuran (121 kg) was added thereto at an internal temperature of 30° C. or lower. Switching to brine cooling, under a nitrogen gas stream, at an internal temperature of from 0 to 10° C., sodium borohydride (7.15 kg, 1.1 M/M) was added thereto, split over 5 hours or longer. After addition of sodium borohydride was finished, the jacket was switched to cold water (4.0° C.) circulation, and the solution was stirred overnight at an internal temperature of from 0 to 10° C. On the next day, at an internal temperature of from 0 to 10° C., sodium borohydride (1.30 kg, 0.2M/M) was added thereto, split over one hour or longer. The jacket was switched to cold water, the internal temperature was heated up to from 20 to 30° C. over three hours or longer, and further, the stirring was carried out overnight at an internal temperature of from 20 to 30° C. On the next day, how the reaction was progressing was checked by HPLC, and since the reaction almost did not progress, the solution was cooled again and sodium borohydride (1.30 kg, 0.2 M/M) was split-added at an internal temperature of from 0 to 10° C. After stirring at an internal temperature of from 0 to 10° C. for one hour or longer, the jacket was switched to cold water circulation and heated up to an internal temperature of from 15 to 25° C. over two hours or longer. After stirring for one hour or longer, it was confirmed by HPLC (Condition 1) that the reaction had ended, and the solution was stirred overnight.

The next day, after an aqueous solution of 48.7% sodium hydroxide (71 kg, 5M/M) was added dropwise thereto at an internal temperature of 50° C. or lower, in continuation, water (133 L) was added dropwise thereto at an internal temperature of 50° C. or lower. Hot water (50 to 80° C.) circulation was started, after stirring at an internal temperature of from 50 to 60° C. for 20 hours or longer, it was confirmed by HPLC (Condition 2) that the reaction had ended.

Next, under a water cooling, water (73 L) was added dropwise thereto. After switching to cold water (15° C.) cooling, [5-(2-aminopyridin-3-yl)isoxazol-3-yl]methanol was added thereto at an internal temperature of from 15 to 30° C., and precipitation of solid was confirmed, water (218 L) was added dropwise thereto, then, under a brine cooling, 35% hydrochloric acid (115 kg) was added dropwise thereto at an internal temperature of from 15 to 30° C., and which was washed there to down with water (3 L). After stirring at an internal temperature of from 15 to 30° C. for five minutes or longer, it was confirmed that a pH of the reaction solution was from 4.00 to 5.00 with a pH meter, and the solution was stirred at an internal temperature of from 15 to 30° C. for one hour or longer. Then, an aqueous solution of 48.7% sodium hydroxide (17.1 kg employment) was added dropwise thereto until a pH of the solution was from 7.00 to 8.00, and the solution was left standing still overnight. On the next day, after stirring and pressure reduction were started and distillation from the condenser was confirmed, hot water (40° C.) circulation was started. Concentration was carried out for one hour or longer under the conditions of hot water (35 to 45° C.), 68 cm Hg or greater level of reduced pressure, and 30° C. or higher internal temperature. The reduced pressure was released under a nitrogen and the solid attached to the reactor wall was washed thoroughly with water (approximately 20 L). The solution was stirred at an internal temperature of from 15 to 30° C. for three hours or longer and was left standing still overnight. On the next day, the internal temperature was confirmed to be within a range of from 15 to 25° C., the slurry solution was solid-liquid separated with a centrifuge, divided in two stages. At each centrifugation, the solid was washed with water (approximately 200 L), after draining, centrifugal separation was carried out for one hour and then the wet solid was taken out into a poly bag. Then, in a shelf dryer, under 45 to 50° C. hot water circulation, the solid was dried under a reduced pressure, so as to obtain the title compound (26.57 kg, yield: 80.9%).

$^1$H-NMR Spectrum (DMSO-d$_6$) δ (ppm):4.54(2H,s), 5.57 (1H,brs), 6.25(2H,brs), 6.71(1H,dd,J=4.8,8.0 Hz), 6.90(1H, s), 7.90(1H,dd,J=1.6,7.6 Hz), 8.09(1H,dd,J=1.6,4.8 Hz).

HPLC condition 1: column: YMC-Pack Pro C18 (5 μm, 150×4.6 mml.D., YMC), mobile phase: acetonitrile/water/ammonium acetate=300/700/1 to 900/100/1 (v/v/w).

HPLC condition 2: column: YMC-Pack ODS-AQ (5 μm, 150×4.6 mml.D., YMC), mobile phase: acetonitrile/water/85% phosphoric acid/sodium 1-octane sulfonate=161.3/838.7/1/1.1 to 900/100/1/1.1 (v/v/v/w).

Manufacturing Examples 8 to 9 are other synthesis methods to Example 5.

Example 8

Synthesis of [5-(2-aminopyridin-3-yl)isoxazol-3-yl]methanol oxalate

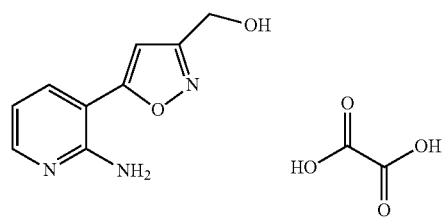 [SMILES: Nc1ncccc1-c1cc(CO)no1 ; O=C(O)C(=O)O]

To a mixture of ethyl 5-{2-[(2,2-dimethylpropanoyl)amino]pyridin-3-yl}isoxazol-3-carboxylate (3.17 g, 10 mmol), ethanol (3 mL) and tetrahydrofuran (10 mL) was added sodium borohydride (0.38 g, 10 mmol) at room temperature, which was stirred overnight under a ice cooling to room temperature. The reaction mixture was divided equally into five, among which one was added to 5N aqueous sodium hydroxide (2 mL), which was stirred overnight at 55° C. To the reaction mixture was added water, which was extracted with a mixture of methyl-tert-butylether and tetrahydrofuran, and oxalic acid (0.18 g, 2 mmol) was added to the organic layer. The precipitated solid was filtered, so as to obtain the title compound (0.39 g) as a white solid.

$^1$H-NMR Spectrum (DMSO-d$_6$) δ (ppm):4.54(2H,s), 6.31 (2H,brs), 6.72(1H,dd,J=4.8,8.0 Hz), 6.89(1H,s), 7.90(1H,dd, J=2.0,8.0 Hz), 8.09(1H,dd,J=2.0,4.8 Hz).

Example 9

Synthesis of [5-(2-aminopyridin-3-yl)isoxazol-3-yl]methanol

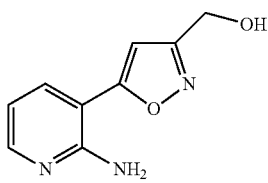 [SMILES: Nc1ncccc1-c1cc(CO)no1]

To a mixture of [5-(2-aminopyridin-3-yl)isoxazol-3-yl]methanol oxalate (0.39 g) and water (2 mL) was added 5N aqueous sodium hydroxide (0.5 mL) at room temperature and the precipitated solid was filtered, so as to obtain the title compound (0.18 g) as a white solid.

$^1$H-NMR Spectrum (DMSO-$d_6$) δ (ppm):4.54(2H,s), 5.57 (1H,brs), 6.25(2H,brs), 6.71(1H,dd,J=4.8,8.0 Hz), 6.90(1H, s), 7.90(1H,dd,J=1.6,7.6 Hz), 8.09(1H,dd,J=1.6,4.8 Hz).

Example 10

Synthesis of 3-[3-(chloromethyl)isoxazol-5-yl]pyridin-2-amine

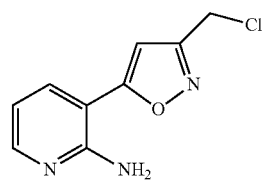 [SMILES: Nc1ncccc1-c1cc(CCl)no1]

To a mixture of [5-(2-aminopyridin-3-yl)isoxazol-3-yl]methanol (0.19 g, 1 mmol) and N,N-dimethyl acetamide (1 mL) was added a mixture of thionyl chloride (0.15 mL, 2 mmol), benzotriazole (0.26 g, 2.2 mmol) and tetrahydrofuran (1 mL) under an ice cooling, which was stirred at room temperature for 30 minutes. To the reaction mixture were added water and 5N aqueous sodium hydroxide to adjust basic, then extracted with ethyl acetate, and the organic layer was washed with saturated sodium chloride water. The solvent was evaporated under a reduced pressure, so as to obtain the title compound (0.21 g) as a pale yellow solid.

$^1$H-NMR Spectrum (DMSO-$d_6$) δ (ppm):4.84(2H,s), 6.31 (2H,brs), 6.72(1H,dd,J=4.8,8.0 Hz), 7.04(1H,s), 7.91(1H,dd, J=1.6,7.6 Hz), 8.11(1H,dd,J=1.2,4.8 Hz).

Example 11

Synthesis of di-tert-butyl{3-[3-(chloromethyl)isoxazol-5-yl]pyridin-2-yl}imidodicarbonate

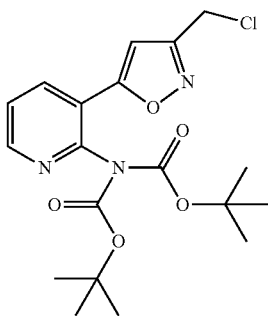 [SMILES: CC(C)(C)OC(=O)N(C(=O)OC(C)(C)C)c1ncccc1-c1cc(CCl)no1]

To a mixture of 3-[3-(chloromethyl)isoxazol-5-yl]pyridin-2-amine (420 mg, 2.01 mmol), 4-dimethyl aminopyridine (26.8 mg, 0.220 mmol), and tetrahydrofuran (2.1 mL) was added di-tert-butyldicarbonate (924 mg, 4.24 mmol) at room temperature, which was stirred. After 25 hours, to the reaction solution was added water and extracted with toluene, then the organic layer was washed with 5% sodium chloride water and the solvent was evaporated under a reduced pressure, so as to obtain the title compound (880 mg) as a pale yellow oily product.

$^1$H-NMR Spectrum (CDCl$_3$) δ (ppm):1.33(18H,s), 4.63 (2H,s), 6.66(1H,s), 7.45(1H,dd,J=4.8,8.0 Hz), 8.30(1H,dd, J=2.0,8.0 Hz), 8.62(1H,dd,J=2.0,4.8 Hz).

Examples 12 to 15 are other synthesis methods to Examples 4 to 5 and Examples 10 to 11.

Example 12

Synthesis of tert-butyl{3-[3-(hydroxymethyl)isoxazol-5-yl]pyridin-2-yl}carbamate

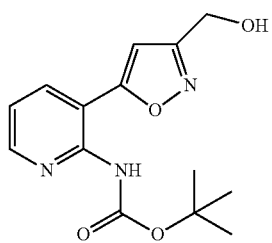 [SMILES: CC(C)(C)OC(=O)Nc1ncccc1-c1cc(CO)no1]

To a mixture of ethyl 5-{2-[(2,2-dimethylpropanoyl)amino]pyridin-3-yl}isoxazol-3-carboxylate (1.59 g, 5 mmol), di-tert-butyl dicarbonate (1.31 g, 6 mmol), and tetrahydrofuran (5 mL) was added 4-dimethylaminopyridine (61 mg, 0.5 mmol) at room temperature, which was stirred at room temperature for one hour and then stirred at 60° C. for six hours. To the reaction mixture were added ethanol (2.5 mL) and sodium borohydride (0.57 g, 15 mmol), which was stirred at 0° C. for 30 minutes and then stirred overnight at room temperature. To the reaction mixture was added water, extracted with ethyl acetate, and the organic layer was washed with water and saturated sodium chloride water. After drying over anhydrous magnesium sulfate and filtering, the solvent was evaporated under a reduced pressure, so as to obtain the title compound (1.60 g).

$^1$H-NMR Spectrum (CDCl3) δ (ppm):1.47(9H,s), 4.83(2H,s), 6.63(1H,s), 7.17(1H,dd,J=4.8,8.0 Hz), 7.58(1H, s), 7.97(1H,dd,J=2.0,8.0 Hz), 8.51(1H,dd,J=2.0,4.8 Hz).

Example 13

Synthesis of tert-butyl{3-[3-(chloromethyl)isoxazol-5-yl]pyridin-2-yl}carbamate

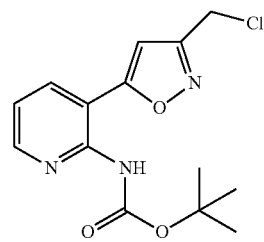 [SMILES: CC(C)(C)OC(=O)Nc1ncccc1-c1cc(CCl)no1]

Under a nitrogen atmosphere, benzotriazole (3.55 g, 29.5 mmol) was dissolved in N,N-dimethylacetamide (10 mL), and thionyl chloride (2.06 mL, 26.8 mmol) was added dropwise thereto under an ice water cooling to prepare a solution of thionyl chloride-benzotriazole (1:1.1) in N,N-dimethylacetamide.

Under a nitrogen atmosphere, tert-butyl {3-[3-(hydroxymethyl)isoxazol-5-yl]pyridin-2-yl}carbamate (781 mg, 2.68 mmol) was dissolved in N,N-dimethylacetamide (2.7 mL). To the solution was added the above solution of thionyl chloride-benzotriazole (1:1.1) in N,N-dimethylacetamide (6 mL, 14.4 mmol) dropwise under an ice water cooling, which was stirred at the same temperature for one hour and then stirred at room temperature. After one hour and 20 minutes, under the ice water cooling, a solution of thionyl chloride-benzotriazole (1:1.1) in N,N-dimethylacetamide (2.2 mL, 5.12 mmol) was added dropwise thereto, and the solution was stirred at room temperature for one hour. Under the ice water cooling, to the reaction solution were added 1N aqueous sodium hydroxide and tert-butylmethylether to adjust basic and then extracted. The organic layer was washed sequentially with 0.5N aqueous sodium hydroxide and 5% sodium chloride water, dried over anhydrous magnesium sulfate and then the solvent was evaporated under a reduced pressure, so as to obtain a crude body of the title compound (953 mg) as a pale yellow oily product.

$^1$H-NMR Spectrum (CDCl$_3$) δ (ppm):1.47(9H,s), 4.65(2H, s), 6.67(1H,s), 7.20(1H,dd,J=4.8,8.0 Hz), 7.44(1H,brs), 8.01 (1H,dd,J=2.0,8.0 Hz), 8.52(1H,dd,J=2.0,4.8 Hz).

Example 14

Synthesis of di-tert-butyl{3-[3-(chloromethyl)isoxazol-5-yl]pyridin-2-yl}imidodicarbonate

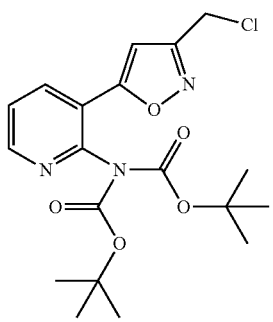 [SMILES: CC(C)(C)OC(=O)N(C(=O)OC(C)(C)C)c1ncccc1-c1cc(CCl)no1]

A crude matter of tert-butyl {3-[3-(chloromethyl)isoxazol-5-yl]pyridin-2-yl}carbamate (1.13 g, 3.17 mmol) was dissolved in tetrahydrofuran (7.0 mL), di-tert-butyl dicarbonate (761 mg, 3.49 mmol) was added thereto under an ice water cooling and washed thereto down with THF (3.0 mL). Then, after 4-dimethylaminopyridine (39.1 mg, 0.317 mmol) was added thereto, the solution was stirred at room temperature. After five hours, under the ice water cooling, to the reaction solution were added ethyl acetate and 5% sodium chloride water and extracted. After the organic layer was washed with 5% sodium chloride water and dried over anhydrous magnesium sulfate, the solvent was evaporated under a reduced pressure. The residue was purified by silica gel column chromatography, so as to obtain the title compound (1.14 g) as a pale yellow solid.

$^1$H-NMR Spectrum (CDCl$_3$) δ (ppm):1.33(18H,s), 4.63 (2H,s), 6.66(1H,s), 7.45(1H,dd,J=4.8,8.0 Hz), 8.30(1H,dd, J=2.0,8.0 Hz), 8.62(1H,dd,J=2.0,4.8 Hz).

Example 15

Synthesis of di-tert-butyl{3-[3-(chloromethyl)isoxazol-5-yl]pyridin-2-yl}imidodicarbonate

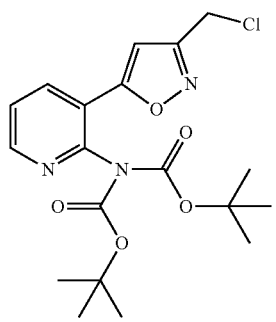 [SMILES: CC(C)(C)OC(=O)N(C(=O)OC(C)(C)C)c1ncccc1-c1cc(CCl)no1]

Under a nitrogen gas stream, [5-(2-aminopyridin-3-yl) isoxazol-3-yl]methanol (26.00 kg, 136.0 mol) and 1,3-dimethyl-2-imidazolidinone (143 kg, 5.5 w/w, a portion was set aside for thorough wash) were added to a 500 L reactor 1 and stirring was started. The solution was stirred at an internal temperature of from 35 to 45° C. for one hour or longer and cooled after dissolution of [5-(2-aminopyridin-3-yl)isoxazol-3-yl]methanol. At an internal temperature of from 5 to 25° C., thionyl chloride (19.40 kg, 163.1 mol, 1.2M/M) was added dropwise thereto. After the dropwise addition was finished, thionyl chloride was thoroughly washed down with the set aside 1,3-dimethyl-2-imidazolidinone, the solution was stirred an internal temperature of from 5 to 25° C. for 12 hours or longer. After the end of the reaction was confirmed by HPLC analysis, an aqueous solution of approximately 36% sodium hydroxide (mixed solution between an aqueous solution of 48% sodium hydroxide (15.9 kg; 190.8 mol, 1.4M/M as sodium hydroxide) and water (5.3 kg, 0.2w/w)) was added dropwise thereto at an internal temperature of from 0 to 25° C., and then ethyl acetate (164 kg, 6.31 w/w) and water (74.2 kg, 2.85 w/w) were added dropwise at an internal temperature of from 15 to 35° C. In addition, after an aqueous solution of approximately 8% sodium hydroxide (mixed solution between a solution of 48% sodium hydroxide (13.6 kg; 163.2 mol, 1.20 M/M as sodium hydroxide) and water (68.0 kg, 2.6 w/w)) was added dropwise thereto at an internal temperature of from 0 to 25° C. and the internal temperature was adjusted to 15 to 30° C., the solution was stirred at the same temperature range for 30 minutes or longer and left standing still for 30 minutes or longer. The lower layer and the upper layer were removed separately, each of the respective ½ weights was added to the 500 L reactor 1 and a 500 L reactor 2.

Post-processing of the 500 L reactor 1 was carried out as described below. After stirring was started and water (52 kg, 2 w/w) was added thereto, an aqueous solution of approximately 8% sodium hydroxide (mixed solution between an aqueous solution of 48% sodium hydroxide (11.3 kg; 135.6 mol, 1.0 M/M as sodium hydroxide) and water (56.5 kg, 2.17 w/w)) was added dropwise little by little at an internal temperature of from 0 to 25° C. to adjust a pH of the lower layer to from 7.00 to 8.50 (actual value: pH7.84). At this time, 35.55 kg of the aqueous solution of approximately 8% sodium hydroxide was used. Then, after the internal temperature was adjusted to 15 to 30° C. and the solution was stirred for 30 minutes or longer, the solution was left standing still overnight. On the next day, after the pH was confirmed again to be pH 7.59, the upper layer and the lower layer were respectively separated, only the lower layer was returned to the 500 L reactor 1, and then ethyl acetate (82 kg, 3.15 w/w) was added thereto. After stirring at an internal temperature of from 15 to 30° C. for five minutes, the solution was left standing still for 30 minutes or longer, and the lower layer (pH7.55) was eliminated. To the upper layer that was left in the reactor were added the separated upper layer and 5% sodium chloride water (mixed solution between sodium chloride (3.3 kg, 0.13 w/w) and water (618 kg, 2.38 w/w)), which was stirred at an internal temperature of from 15 to 30° C. for five minutes, then left standing still for 30 minutes or longer and the lower layer (pH8.23) was eliminated. Furthermore, water (65 kg, 2.5 w/w) was added thereto, the solution was stirred at an internal temperature of from 15 to 30° C. for five minutes and then left standing still overnight, and the lower layer (pH7.04) was eliminated.

The post-processing of the 500 L reactor 2 was conducted concurrently with the operations for the 500 L reactor 1, the same procedure was carried out.

Next, the upper layer of the 500 L reactor 2 was transferred to the 500 L reactor 1, and the solution was concentrated under a reduced pressure at 45 to 55° C. hot water and −0.070 to −0.085 MPa level of the reduced pressure until the content solution was approximately 200 L. Ethyl acetate (141 kg, 5.42 w/w) was added therein, and the solution was concentrated again under a reduced pressure with the same conditions. After this operation was repeated further twice, before and after the 4$^{th}$ time addition of ethyl acetate (141 kg, 5.42 w/w), the 3-[3-(chloromethyl)isoxazol-5-yl]pyridin-2-amine content in the solution was checked by HPLC analysis, the 3-[3-(chloromethyl)isoxazol-5-yl]pyridin-2-amine content (23.35 kg, 111.4 mol) in the solution and the yield thereof (81.9%) were calculated. Then, concentration under a reduced pressure was carried out once more with the same conditions until the 3-[3-(chloromethyl)isoxazol-5-yl]pyridin-2-amine content was 10.0 to 13.0% to obtain a solution of 3-[3-(chloromethypisoxazol-5-yl]pyridin-2-amine in ethyl acetate.

Under a nitrogen gas stream, the solution of 3-[3-(chloromethyl)isoxazol-5-yl]pyridin-2-amine in ethyl acetate (containing the total amount obtained in the previous step, 23.35 kg (111.4 mol)) inside the 500 L reactor 1 was stirred, di-tert-butyl dicarbonate (53.47 kg, 245.0 mol, 2.2 M/M) was added thereto at an internal temperature of from 15 to 25° C. and which was washed thereto down with ethyl acetate (2 kg). A solution of 4-dimethyl aminopyridine in ethyl acetate (mixed solution of 4-dimethylaminopyridine (0.409 kg, 3.35 mol, 0.03 M/M) and ethyl acetate (8 kg)) prepared beforehand was added therein, and after washing down with ethyl acetate (1 kg), the solution was stirred at an internal temperature of from 10 to 30° C. for 22 hours or longer. After checking the end of the reaction by HPLC analysis, 1,3-dimethyl-2-imidazolidinone (50 kg, 2.12 w/w) was added thereto. The solution was concentrated under a reduced pressure at 45 to 55° C. hot water circulation, until −0.092 MPa or greater level of the reduced pressure and liquid distillation weakened, and after checking by GC analysis that the ethyl acetate content was 7.0%, the reactor was cooled to an internal temperature of 30° C. or lower, and the solution was left standing still overnight. On the next day, to the concentration residue was added methanol (111 kg, 4.74 w/w), which was stirred for 10 minutes or longer, and it was confirmed that no solid had precipitated, the solution was divided into two fractions. Next, the solutions divided into two fractions were added respectively to the 500 L reactors 1 and 2, and respectively washed thereto down with methanol (9 kg each, 0.4 w/w each). In so doing, as a result of analyzing by HPLC the solution prior to the two fraction division (225.65 kg), the target di-tert-butyl {3-[3-(chloromethyl)isoxazol-5-yl]pyridin-2-yl}imidodicarbonate content was 19.37%, and the weight of di-tert-butyl {3-[3-(chloromethyl)isoxazol-5-yl]pyridin-2-yl}imidodicarbonate contained was 43.71 kg (106.6 mol, yield: 95.7%).

For the 500 L reactor 1 the processing was as described below. After stirring was started, at an internal temperature of from 35 to 45° C., water (35 kg, 1.5 w/w) was added dropwise thereto over 30 minutes or longer, and di-tert-butyl {3-[3-(chloromethyl)isoxazol-5-yl]pyridin-2-yl}imidodicarbonate (0.010 kg) was added thereto at an internal temperature of from 35 to 40° C. After stirring at an internal temperature of from 35 to 40° C. for 30 minutes or longer, precipitation of solid was checked, and the solution was stirred further at the same temperature range for one hour or longer. Then, after water (three times 35 kg, 1.5 w/w each) was added dropwise thereto over 30 minutes or longer at an internal temperature of from 35 to 45° C., the reactor was cooled to an internal temperature of from 5 to 15° C. over 3 hours or longer, and the solution was stirred at the same temperature range for 12 hours or longer. Solid-liquid separation was carried out with a centrifuge dividing into two times, and the cake was washed with hydrous methanol (mixed solution of methanol (each time 7 kg, 0.3 w/w) and water (each time 27 kg, 1.14 w/w)). After washing was finished, centrifugal separation was carried out for 30 minutes or longer to obtain a wet solid of the title compound (25.80 kg). This wet solid was loaded into a mixing type vacuum dryer and vacuum dried at an external temperature from 45 to 55° C. for 24 hours or longer to obtain the title compound (21.09 kg) as a pale yellow solid.

The operation for the 500 L reactor 2 was carried out concurrently with the above, the same operations were performed, so as to obtain the title compound (21.22 kg) as a pale yellow solid.

Accordingly, the title compound (42.31 kg, yield: 92.7%) was obtained.

$^1$H-NMR Spectrum (CDCl$_3$) δ (ppm):1.33(18H,s), 4.63 (2H,s), 6.66(1H,s), 7.45(1H,dd,J=4.8,8.0 Hz), 8.30(1H,dd, J=2.0,8.0 Hz), 8.62(1H,dd,J=2.0,4.8 Hz).

HPLC conditions: column: YMC-Pack Pro C18 (5 μm, 150×4.6 mmI.D., YMC), mobile phase: acetonitrile/water/ammonium acetate=300/700/1 to 900/100/1 (v/v/w).

GC Conditions: column: DB-624 (30 m, 0.53 mmI.D., Film 3 μm, Agilent).

Manufacturing Example 6

Ethyl 5-{2-[(2,2-dimethyl propoxy carbonyl)amino]pyridin-3-yl}isoxazol-3-carboxylate

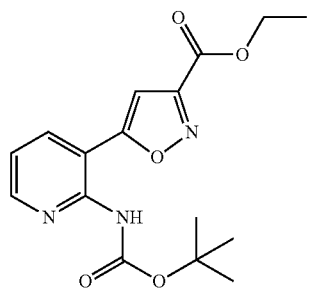 [SMILES: CCOC(=O)c1cc(-c2cccnc2NC(=O)OC(C)(C)C)on1]

To a mixture of 4-methylen-2-oxo-4H-pyrido[2,3-d][1,3] oxazin-1-carboxylic acid tert-butyl ester (2.71 g, 10.37 mmol), which was synthesized according to the methods described in the pamphlet of the International Publication WO 08/136279, Specifications, Preparation Example 3-3-1, triethylamine (4.2 mL, 30 mmol) and tetrahydrofuran (30 mL) was added ethyl 2-chloro-2-(hydroxyimino)acetate (4.5 g, 30 mmol) at 0° C. over two hours and then stirred at room temperature for 14 hours. To the reaction mixture was added water, extracted with ethyl acetate and the organic layer was washed with water and saturated sodium chloride water. After drying over magnesium sulfate and filtering, the solvent was evaporated under a reduced pressure. The residue was suspended and washed with a 1:1 mixture of n-hexane and ethyl acetate, so as to obtain the title compound (1.56 g).

1H-NMR Spectrum (CDCl3) δ (ppm):1.44(3H,t,J=6.8 Hz), 1.46(9H,s), 4.47(4H,q,J=7.2 Hz), 6.95(1H,s), 7.22(1H, dd,J=4.8,8.0 Hz), 7.42(1H,bs), 8.05(1H,dd,J=2.0,8.0 Hz), 8.52(1H,dd,J=2.0,4.8 Hz).

Example 16

Ethyl 5-{2-[bis (2,2-dimethyl propoxy carbonyl) amino]pyridin-3-yl}isoxazol-3-carboxylate

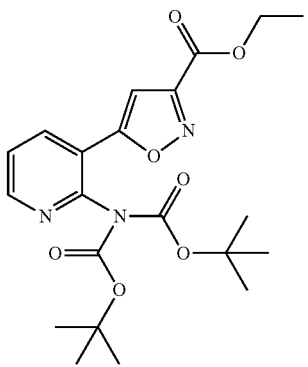 [SMILES: CCOC(=O)c1cc(-c2cccnc2N(C(=O)OC(C)(C)C)C(=O)OC(C)(C)C)on1]

To a mixture of ethyl 5-{2-[(2,2-dimethylpropoxycarbonyl)amino]pyridin-3-yl}isoxazol-3-carboxylate (1.46 g, 4.38 mmol), di-tert-butyl dicarbonate (1.46 g, 6.69 mmol) and tetrahydrofuran (25 mL) was added 4-dimethylaminopyridine (30 mg, 0.25 mmol) at room temperature, which was stirred at room temperature for 14 hours. To the reaction mixture was added water, extracted with ethyl acetate, and the organic layer was washed with water and saturated sodium chloride water. After drying over magnesium sulfate and filtering, the solvent was evaporated under a reduced pressure and the residue was purified by silica gel column chromatography (hexane:ethyl acetate=3:1 then 1:1), so as to obtain the title compound (1.96 g).

$^1$H-NMR Spectrum (CDCl3) δ (ppm):1.36(18H,s), 1.46 (3H,t,J=6.8 Hz), 4.47(4H,q,J=6.8 Hz), 6.93(1H,s), 7.46(1H, dd,J=4.8,7.6 Hz), 8.29(1H,d,J=7.6 Hz), 8.64(1H,d,J=4.8 Hz).

Example 17

Di-tert-butyl{3-[3-(hydroxymethyl)isoxazol-5-yl] pyridin-2-yl}imidodicarbonate

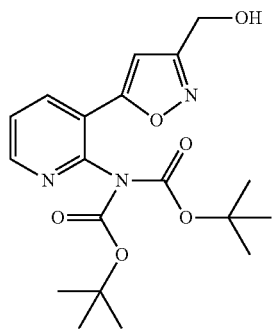 [SMILES: CC(C)(C)OC(=O)N(C(=O)OC(C)(C)C)c1ncccc1-c1cc(CBr)no1]

To a mixture of ethyl 5-{2-[bis(2,2-dimethylpropoxycarbonyl)amino]pyridin-3-yl}isoxazol-3-carboxylate (1.73 g, 4 mmol), ethanol (5 mL) and tetrahydrofuran (5 mL) was added sodium borohydride (0.15 g, 4 mmol) at 0° C., which was stirred at room temperature for one hour. Sodium borohydride (0.15 g, 4 mmol) was further added thereto and the solution was stirred at room temperature for three hours. To the reaction mixture was added water, extracted with ethyl acetate and the organic layer was washed with water and saturated sodium chloride water. After drying over anhydrous magnesium sulfate and filtering, the solvent was evaporated under a reduced pressure. The residue was added with a mixture of n-hexane-ethyl acetate (1:1), suspended and stirred, and then filtered, so as to obtain the title compound (1.02 g).

$^1$H-NMR Spectrum (CDCl$_3$) δ (ppm):1.33(18H,s), 4.81 (2H,s), 6.60(1H,s), 7.43(1H,dd,J=4.8,8.0 Hz), 8.27(1H,dd, J=2.0,8.0 Hz), 8.60(1H,dd,J=2.0,4.8 Hz)

Example 18

Di-tert-butyl{3-[3-(bromomethyl)isoxazol-5-yl]pyridin-2-yl}imidodicarbonate

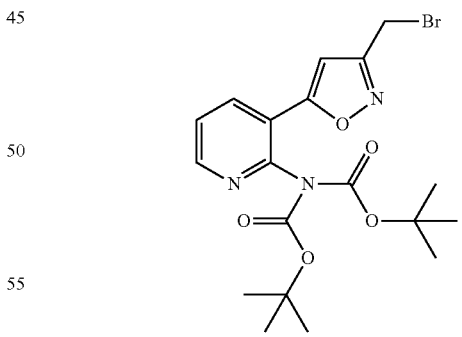

To a mixture of di-tert-butyl {3-[3-(hydroxymethyl)isoxazol-5-yl]pyridin-2-yl}imidodicarbonate (0.78 g, 2 mmol), triethylamine (1.95 mL, 14 mmol) and 1,2-dimethoxyethane (10 mL) was added phosphorus tribromide (0.37 mL, 4 mmol) dropwise at 0° C., which was stirred at room temperature for two hours, and then stirred at 50° C. for 30 minutes. The reaction mixture was cooled to 0° C., then water was added thereto and extracted with ethyl acetate, and the organic layer was washed with saturated sodium chloride water. After drying over anhydrous magnesium sulfate and filtering, the solvent was evaporated under a reduced pressure, the residue was purified by silica gel column chromatography, so as to obtain the title compound (0.14 g).

¹H-NMR Spectrum (CDCl3) δ (ppm):1.33(18H,s), 4.45 (2H,s), 6.63(1H,s), 7.43(1H,dd,J=4.8,8.0 Hz), 8.28(1H,dd, J=2.0,8.0 Hz), 8.61(1H,dd,J=2.0,4.8 Hz).

Example 19

(5-{2-[bis(tert-butoxycarbonyl)amino]pyridin-3-yl}isoxazol-3-yl)methyl 4-methylbenzenesulfonate

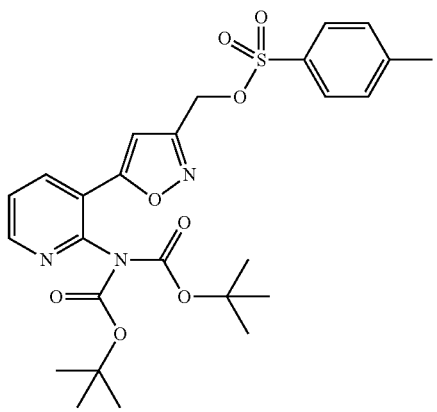 [SMILES: Cc1ccc(S(=O)(=O)OCc2cc(-c3cccnc3N(C(=O)OC(C)(C)C)C(=O)OC(C)(C)C)on2)cc1]

A mixture of di-tert-butyl {3-[3-(hydroxymethyl)isoxazol-5-yl]pyridin-2-yl}imidocarbonate (0.170 g, 0.434 mmol), triethylamine (91 µL, 0.651 mmol), 4-dimethylaminopyridine (5 mg, 0.043 mmol), p-toluenesulfonyl chloride (0.104 g, 0.543 mmol), and tetrahydrofuran (10 mL) was stirred at room temperature. After 15 hours, triethylamine (40 µL, 0.287 mmol) and 50 mg (0.262 mmol) of p-toluenesulfonyl chloride (50 mg, 0.262 mmol) were added thereto and stirred at room temperature. After 5 hours and 30 minutes, water was added to the reaction mixture, which was extracted with ethyl acetate, and the organic layer was washed first with water and then with saturated sodium chloride water. After drying over anhydrous magnesium sulfate and filtering, the solvent was evaporated under a reduced pressure, the residue was purified by silica gel column chromatography, so as to obtain the titled compound (0.151 g) as a white powder.

¹H-NMR Spectrum (CDCl3)δ(ppm):1.33(18H,s), 2.45(3H,s), 5.14(2H,s), 6.61(1H,s), 7.38(2H,d,J=8.0 Hz), 7.43(1H,dd,J=4.8,8.0 Hz), 7.83(2H,d,J=8.0 Hz), 8.22(1H,dd, J=2.0,8.0 Hz), 8.61(1H,dd,J=2.0,4.8 Hz).

Manufacturing Example 7

Synthesis of 2-[(4-bromobenzyl)oxy]pyridine

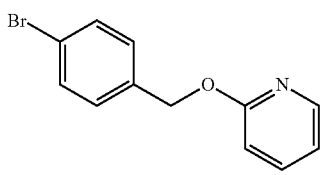 [SMILES: Brc1ccc(COc2ccccn2)cc1]

To a solution of 4-bromobenzyl alcohol (18 g, 94.3 mmol) in dimethylsulfoxide (85 mL) was added potassium tert-butoxide (11.5 g, 99 mmol) little by little under a nitrogen atmosphere at room temperature, which was stirred for 10 minutes. To this solution was added 2-fluoropyridine (12.3 g, 123 mmol) dropwise over 30 minutes under a water bath cooling. After stirring at room temperature for two hours, ethyl acetate and 5% sodium chloride water were added, and extracted. After the organic layer was washed sequentially with water and 5% sodium chloride water, the solvent was evaporated under a reduced pressure, so as to obtain the title compound (24.3 g) as a yellow oily product.

¹H-NMR Spectrum (CDCl₃) δ (ppm):5.33(2H,s), 6.87-6.70(1H,m), 6.98-7.02(1H,m), 7.38-7.44(2H,m), 7.55-7.60 (2H,m), 7.71-7.76(1H,m), 8.15-8.18(1H,m).

Manufacturing Example 8 is the other synthesis method to Manufacturing Example 7.

Manufacturing Example 8

Synthesis of 2-[(4-bromobenzyl)oxy]pyridine

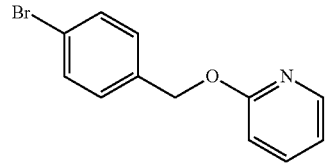

Under a nitrogen atmosphere, to a solution of 4-bromobenzyl alcohol (600 g, 3.21 mol) and 2-fluoropyridine (343 g, 3.53 mol) in tetrahydrofuran (1069 mL) was added a solution of potassium tert-butoxide (396 g, 3.53 mol) in tetrahydrofuran (3208 mL) (63 min, 9.2 to 20.5° C.) dropwise under a 7° C. cooling. After stirring at 22° C. for three hours, an aqueous solution of 5% sodium bicarbonate (prepared from sodium bicarbonate: 160 g and water: 3208 mL) was added thereto dropwise (20 min, 21.0 to 23.9° C.). Then, heptane (3220 mL) was added thereto and extracted, the organic layer was washed with water (800 mL). The organic layer was concentrated under a reduced pressure (to approximately 3200 mL), ethanol (1604 mL) was added thereto and concentrated under a reduced pressure (to approximately 3200 mL). Then, to the layer was added heptane (3200 mL), concentrated under a reduced pressure, heptane (3200 mL) was further added thereto and concentrated under a reduced pressure, so as to obtain a solution of the title compound in heptane (2603 g, containing 789 g of the target product) as a brown oily product (yield: 93.2%).

¹H-NMR Spectrum (CDCl₃) δ (ppm):5.33(2H,s), 6.87-6.70(1H,m), 6.98-7.02(1H,m), 7.38-7.44(2H,m), 7.55-7.60 (2H,m), 7.71-7.76(1H,m), 8.15-8.18(1H,m).

Example 20

Synthesis of {4-[(pyridin-2-yloxy)methyl]phenyl}boronic acid

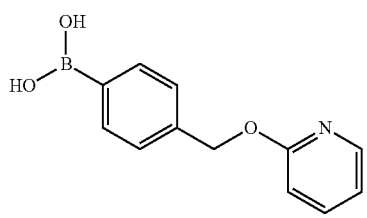 [SMILES: OB(O)c1ccc(COc2ccccn2)cc1]

Under a nitrogen atmosphere, a solution of 2-[(4-bromobenzyl)oxy]pyridine (50 g, 190 mmol) in tetrahydrofuran (200 mL) was cooled to −78° C. and a 2.6M n-butyllithium hexane solution (88 mL, 228 mmol) was added thereto dropwise. After stirring for 45 minutes, trimethoxy borane (29.6 g, 285 mmol) was added thereto dropwise at the same temperature. After 30 minutes, a saturated aqueous solution of ammonium chloride and water were added thereto for quenching, and the solution was extracted with ethyl acetate. After the organic layer was washed with a mixture of saturated aqueous solution of ammonium chloride and saturated sodium chloride water and dried over anhydrous sodium sulfate, the solvent was evaporated under a reduced pressure. To the residue was added acetonitrile (200 mL), followed by suspending and stirring at 70° C. for 30 minutes, then, cooled, and stirred overnight at 4° C. The precipitated solid was filtered, so as to obtain the title compound (11.2 g) as a white solid.

$^1$H-NMR Spectrum (CDCl$_3$) δ (ppm):4.62(2H,s), 5.42(2H,s), 6.83(1H,d,J=8.4 Hz), 6.87-6.92(1H,m), 7.50(2H,d,J=8.0 Hz), 7.57-7.62(1H,m), 7.75(2H,d,J=8.0 Hz), 8.16-8.19(1H,m).

Example 21

Synthesis of 2-{[4-(5,5-dimethyl-1,3,2-dioxaborinan-2-yl)benzyl]oxy}pyridine

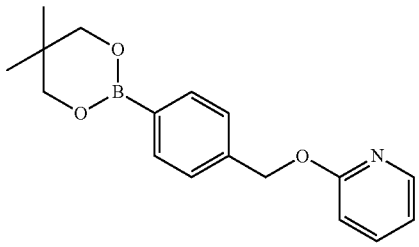 [SMILES: CC1(C)COB(c2ccc(COc3ccccn3)cc2)OC1]

To a solution of 2-[(4-bromobenzyl)oxy]pyridine (789 g, 2.99 mol) in heptane (2603 g) were added heptane (939 mL) and tetrahydrofuran (1199 mL), which was cooled slowly with dry ice/ethanol bath under a nitrogen atmosphere, while stirring. After 45 minutes, cooling was stopped and 2-[(4-bromobenzyl)oxy]pyridine (0.9 g) was added thereto at an internal temperature of −12° C. Cooling was resumed, with cooling at −20° C./h. Approximately 3 hours later, 1.66M n-butyllithium hexane solution (1980 mL, 3.29 mol) was added thereto dropwise (80 min,−67.0 to 61.4° C.). After stirring for 0.5 hours, at the same temperature, triisopropoxy borane (674 g, 3.56 mol) was added thereto dropwise (134min, −68.2 to 60.3° C.). At the same temperature, after stirring for 0.5 hours, switching to an ice water bath cooling, the solution was stirred overnight (external temperature: 0° C.). On the next day, water (5600 mL) was added thereto dropwise, the solution was transferred to a separator vessel and was extracted into the aqueous layer (pH: 11.2). Ethyl acetate (4800 mL) was added thereto and concentrated hydrochloric acid (approximately 280 mL) was added thereto dropwise (at an internal temperature of 20° C. or lower) while stirring, to adjust the solution to pH: 7.1. The organic layer was separated and washed with 5% sodium chloride water (approximately 900 g) and then concentrated under a reduced pressure. To the residue was added isopropyl alcohol (3300 mL), concentrated under a reduced pressure, isopropyl alcohol (3300 mL) was further added thereto and concentrated under a reduced pressure to obtain a solution of {4-[(pyridin-2-yloxy)methyl]phenyl}boronic acid (646 g) in isopropyl alcohol (2671 g) (yield: 94.4%). The obtained solution was heated to 60° C., which was added to a container containing 2,2-dimethyl-1,3-propanediol (354 g, 3.41 mol) while eliminating insoluble matter by suction-filtration, and then which was washed thereto down with isopropyl alcohol (685 mL). After confirming dissolution, the solution was stirred at a bath temperature of 20° C. and crystal precipitation was observed at an internal temperature of 28.8° C. After 1.5 hours, the bath temperature was set to −20° C., and the solution was stirred overnight. The precipitated crystal was filtered, and the crystal was washed with a small amount of isopropyl alcohol cooled to 0° C. The crystal was dried under a reduced pressure, so as to obtain the title compound (779 g) as a white crystal (yield: 92.2%).

$^1$H-NMR Spectrum (DMSO-d$_6$) δ (ppm):0.94(6H,s), 3.74 (4H,s), 5.35(2H,s), 6.87(1H,d,J=8.4 Hz), 6.96-7.00(1H,m), 7.39(2H,d,J=8.0 Hz), 7.67-7.74(3H,m), 8.14-8.17(1H,m).

Example 22

Synthesis of di-tert-butyl[3-(3-{4[(pyridin-2-yloxy)methyl]benzyl}isoxazol-5-yl)pyridin-2-yl]imidodicarbonate

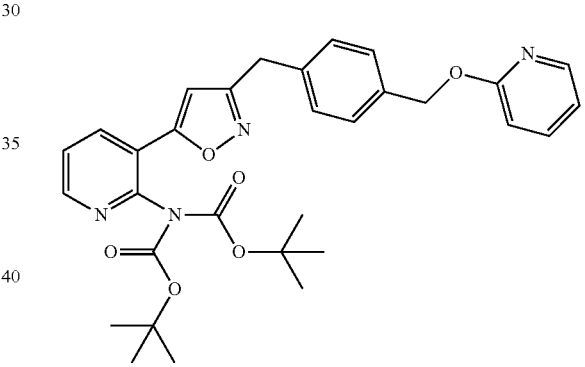

Under nitrogen atmosphere, to a mixture of di-tert-butyl {3-[3-(chloromethyl)isoxazol-5-yl]pyridin-2-yl}imidodicarbonate (164 mg, 0.40 mmol), {4-[(pyridin-2-yloxy)methyl]phenyl}boronic acid (138 mg, 0.60 mmol), cesium carbonate (391 mg, 1.20 mmol), copper(I) iodide (3.9 mg, 5 mol %) and 1,2-dimethoxyethane (2.0 mL) was added [1,1'-bis(diphenylphosphino)ferrocene]dichloropalladium (II) dichloromethane complex (16.4 mg, 5 mol %), which was stirred at 80° C. for 1.5 hours. {4-[(Pyridin-2-yloxy)methyl] phenyl}boronic acid (46 mg, 0.20 mmol) was added thereto and the solution was further stirred for 4.5 hours. After cooling, ethyl acetate and 5% sodium chloride solution were added thereto, insoluble matter was filtered out, then, the filtrate was transferred to a separatory funnel and separated. After the organic layer was washed with 5% sodium chloride water and dried over anhydrous magnesium sulfate, the solvent was evaporated under a reduced pressure. The residue was purified by silica gel column chromatography, so as to obtain the title compound (173 mg) as a pale yellow oily product.

$^1$H-NMR Spectrum (CDCl$_3$) δ (ppm):1.23(9H,s), 4.05(2H, s), 5.34(2H,s), 6.32(1H,s), 6.76-6.79(1H,m), 6.86-6.90(1H, m), 7.28(2H,d, J=8.0 Hz), 7.38-7.43(3H,m), 7.55-7.60(1H, m), 8.15-8.18(1H,m), 8.27(1H,dd,J=2.0,8.0 Hz), 8.57(1H, dd,J=2.0,7.6 Hz).

Example 23

3-(3-(4-pyridin-2-yloxymethyl)-benzyl)-isoxazol-5-yl)-pyridin-2-ylamine

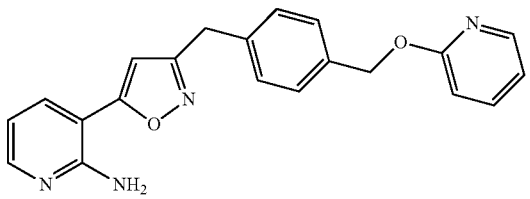 [SMILES: Nc1ncccc1-c1cc(Cc2ccc(COc3ccccn3)cc2)no1]

Di-tert-butyl [3-(3-{4[(pyridin-2-yloxy)methyl]benzyl}isoxazol-5-yl)pyridin-2-yl]imidodicarbonate (28.8 mg, 51.6 μmol) was dissolved in acetonitrile (0.6 mL), concentrated hydrochloric acid (60 μL, 690 μmol) was added thereto dropwise under an ice water cooling, which was stirred at the same temperature for one hour. Concentrated hydrochloric acid (140 μL, 1.61 mmol) was further added thereto dropwise and the solution was stirred at the same temperature for one hour and at 20° C. for 3.5 hours. Under an ice water cooling, to the reaction solution were added 0.5N aqueous sodium hydroxide and ethyl acetate and extracted. After the organic layer was washed with 5% sodium chloride water and dried over anhydrous magnesium sulfate, the solvent was evaporated under a reduced pressure, so as to obtain the title compound (18.3 mg) as a pale yellow oily product.

$^1$H-NMR Spectrum (CDCl$_3$) δ (ppm):4.07(2H,s), 5.37(2H, s), 5.42(2H,brs), 6.25(1H,s), 6.71(1H,dd,J=5.2,7.6 Hz), 6.80 (1H,d,J=8.4 Hz), 6.87-6.91(1H,m), 7.30(2H,d,J=7.6 Hz), 7.44(2H,d,J=7.6 Hz), 7.56-7.61(1H,m), 7.70(1H,dd,J=2.0, 7.6 Hz), 8.14(1H,dd,J=2.0,4.8 Hz), 8.16-8.19(1H,m).

Examples 24 and 25 are other synthesis methods to Examples 22.

Example 24

Synthesis of di-tert-butyl [3-(3-{4-[(pyridin-2-yloxy)methyl]benzyl}isoxazol-5-yl)pyridin-2-yl]imidodicarbonate

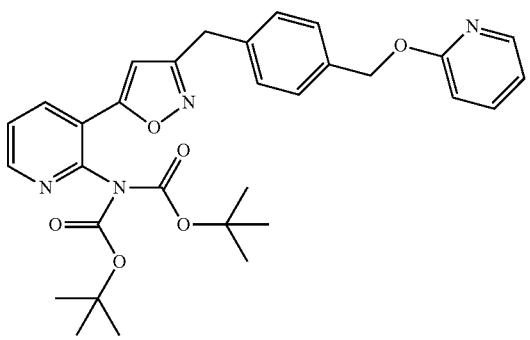 [SMILES: CC(C)(C)OC(=O)N(C(=O)OC(C)(C)C)c1ncccc1-c1cc(Cc2ccc(COc3ccccn3)cc2)no1]

Under a nitrogen atmosphere, to a mixture of di-tert-butyl {3-[3-(bromomethyl)isoxazol-5-yl]pyridin-2-yl}imidodicarbonate (68 mg, 0.15 mmol), {4-[(pyridin-2-yloxy)methyl]phenyl}boronic acid (34 mg, 0.15 mmol), potassium phosphate (35 mg, 0.17 mmol), triphenylphosphine (7.9 mg, 0.03 mmol), and toluene (1.0 mL) was added palladium acetate (1.7 mg, 5 mol %), which was stirred for 16 hours at 90° C. After cooling, ethyl acetate and water were added thereto, and the mixture was transferred to a separatory funnel and separated. The organic layer was washed with saturated sodium chloride solution and then dried over anhydrous magnesium sulfate, the solvent was evaporated under a reduced pressure. The residue was purified by silica gel column chromatography, so as to obtain a mixture of the titled compound, di-tert-butyl {3-[3-(bromomethyl)isoxazol-5-yl] pyridin-2-yl}imidodicarbonate, and di-tert-butyl [3-(3-methylisoxazol-5-yl)pyridin-2-yl]imidodicarbonate (54 mg:molar ratio of 53:36:11), as a yellow oil.

$^1$H-NMR Spectrum (CDCl$_3$)δ(ppm):1.23(9H,s), 4.05(2H, s), 5.34(2H,s), 6.32(1H,s), 6.76-6.79(1H,m), 6.86-6.90(1H, m), 7.28(2H,d,J=8.0 Hz), 7.38-7.43(3H,m), 7.55-7.60(1H, m), 8.15-8.18(1H,m), 8.25-8.30(1H,m), 8.57(1H,dd,J=2.0, 7.6 Hz).

Example 25

Synthesis of di-tert-butyl [3-(3-{4-[(pyridin-2-yloxy)methyl]benzyl}isoxazol-5-yl)pyridin-2-yl]imidodicarbonate

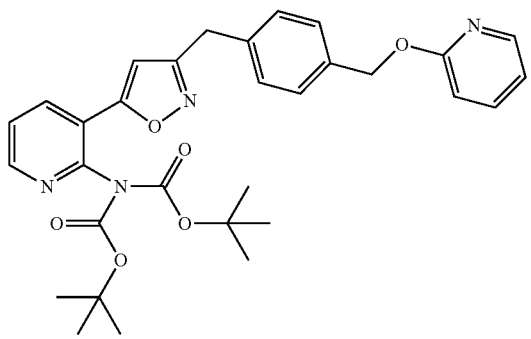 [SMILES: CC(C)(C)OC(=O)N(C(=O)OC(C)(C)C)c1ncccc1-c1cc(Cc2ccc(COc3ccccn3)cc2)no1]

Under a nitrogen atmosphere, to a mixture of (5-{2-[bis(tert-butoxycarbonyl)amino]pyridin-3-yl}isoxazol-3-yl)methyl 4-methylbenzenesulfonate (82 mg, 0.15 mmol), {4-[(pyridin-2-yloxy)methyl]phenyl}boronic acid (34 mg, 0.15 mmol), potassium phosphate (35 mg, 0.17 mmol), triphenylphosphine (7.9 mg, 0.03 mmol), and toluene (1.0 mL) was added palladium acetate (1.7 mg, 5 mol %), which was stirred for 16 hours at 90° C. After cooling, ethyl acetate and water were added thereto, and the mixture was transferred to a separatory funnel and separated. The organic layer was washed with saturated sodium chloride solution and then dried over anhydrous magnesium sulfate, the solvent was evaporated under a reduced pressure. The residue was purified by silica gel column chromatography, so as to obtain a mixture of the titled compound, (5-{2-[bis(tert-butoxycarbonyl)amino]pyridin-3-yl}isoxazol-3-yl)methyl 4-methyl benzenesulfonate, and di-tert-butyl [3-(3-methylisoxazol-5-yl)pyridin-2-yl]imidodicarbonate (63 mg:molar ratio of 59:33: 8), as a pale yellow oil.

$^1$H-NMR Spectrum (CDCl$_3$)δ(ppm):1.23(9H,s), 4.05(2H, s), 5.34(2H,s), 6.32(1H,s), 6.76-6.79(1H,m), 6.86-6.90(1H, m), 7.28(2H,d,J=8.0 Hz), 7.38-7.43(3H,m), 7.55-7.60(1H, m), 8.15-8.18(1H,m), 8.27(1H,dd,J=2.0,8.0 Hz), 8.57(1H, dd,J=2.0,7.6 Hz).

Examples 26 to 27 are other synthesis methods to Examples 22 to 23.

Example 26

Synthesis of di-tert-butyl[3-(3-{4[(pyridin-2-yloxy) methyl]benzyl}isoxazol-5-yl)pyridin-2-yl]imidodicarbonate

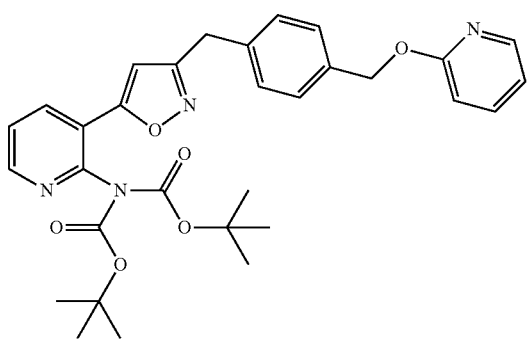 [SMILES: CC(C)(C)OC(=O)N(C(=O)OC(C)(C)C)c1ncccc1-c1cc(Cc2ccc(COc3ccccn3)cc2)no1]

The operation of the first batch was carried out as described below. Under a nitrogen gas stream, after di-tert-butyl {3-[3-(chloromethypisoxazol-5-yl]pyridin-2-yl}imidodicarbonate (20.80 kg, 50.75 mol), 2-{[4-(5,5-dimethyl-1,3,2-dioxaborinan-2-yl)benzyl]oxy}pyridine (19.61 kg, 66.00 mol, 1.30 M/M), (oxydi-2,1-phenylene)bis(diphenylphosphine) (1.367 kg, 2.54 mol, 0.05 M/M), potassium carbonate (9.11 kg, 65.91 mol, 1.30 M/M) were added to a 500 L reactor 2 which was nitrogen-substituted beforehand, the interior of the reactor was nitrogen-substituted again, N,N-dimethyl formamide (147 kg, 7.08 w/w) was added thereto and stirring was started. Then, after maintaining at an internal temperature of from 15 to 25° C. and a level of the reduced pressure of −0.090 MPa or greater for three to five minutes maintenance, the reduced pressure was released with nitrogen. This operation was repeated five times to degas the solution. After degassing was finished, solution of palladium acetate in N,N-dimethyl formamide (mixed solution of palladium acetate (0.570 kg, 2.54 mol, 0.05 M/M) and degassed N,N-dimethyl formamide (9.8 kg, 0.5 w/w, a portion of which was set aside for thorough wash)) was added thereto, and washed thereto down with the set aside degassed N,N-dimethyl formamide. Next, after stirring for 10 minutes, immediately degassed water (10.4 kg, 0.5 w/w) was added thereto dropwise at an internal temperature of from 20 to 30° C., and the operation of reducing the pressure to −0.087 MPa level of the reduced pressure and releasing the reduced pressure with nitrogen was repeated three times. Thereafter, hot water at approximately 60° C. was circulated quickly to adjust the internal temperature to from 55 to 65° C. and the solution was stirred for three hours from the start of the heating. After the end of the reaction was confirmed by HPLC analysis, toluene (90 kg, 4.34 w/w) was added thereto at an internal temperature of from 0 to 25° C. and water (156 kg, 7.5 w/w) was added thereto dropwise at the same temperature range. Then, after stirring at an internal temperature of from 15 to 30° C. for 30 minutes, the solution was left standing still for 30 minutes or longer standing, and the lower layer was eliminated. To the upper layer inside of the reactor was added water (104 kg, 5.0 w/w), which was stirred at an internal temperature of from 15 to 30° C. for five minutes, then left standing still overnight, and only the lower layer containing no insoluble matter was eliminated. The upper layer and the lower layer containing insoluble matter were filtered with Celite 503 RV (2.8 kg, 0.135 w/w) under pressure by a filtration device, and the reactor and the filtration device were pour-washed with toluene (18.0 kg, 0.867 w/w, a portion was set aside for flushing and thorough washing). The obtained filtrate and washes were returned to the 500 L reactor 2 and washed thereto down with the previously set aside toluene. Subsequently, after the internal temperature was adjusted to 15 to 30° C., the solution was left standing still for 30 minutes or longer, and the lower layer was eliminated. After the stirring speed was adjusted to approximately maximum and n-heptane (152 kg, 7.32 w/w) was added thereto dropwise over one hour or longer at an internal temperature of from 15 to 30° C., the solution was stirred at the same temperature range for two hours or longer. Then, after thiocyanuric acid (0.90 kg, 5.08 mol, 0.1 M/M) was added thereinto with divided fractions over 30 minutes or longer at an internal temperature of from 15 to 30° C., the solution was stirred at the same temperature range for one hour or longer. Once more, thiocyanuric acid (0.90 kg, 5.08 mol, 0.1M/M) was added thereinto with divided fractions over 30 minutes or longer at an internal temperature of from 15 to 30° C. and the solution was stirred overnight at the same temperature range. After overnight stirring, the solution in the reactor was filtered with activated carbon by a filtration device which was prepared beforehand, and the reactor and the filtration device were washed thoroughly with a mixed solution of n-heptane-toluene (mixed solution of n-heptane (130 kg) and toluene (83 kg), a portion of which was set aside for wetting the activated carbon (Seisei Shirasagi)). After adding thiocyanuric acid (1.80 kg, 10.16 mol, 0.2M/M) thereinto once more, filtration with activated carbon was carried out using the same amount of Celite 503 RV, activated carbon (Seisei Shirasagi) and mixed solution of n-heptane-toluene. The obtained filtrate and washes were added to the 500 L reactor 1, which was concentrated under a reduced pressure and hot water circulation at 40 to 70° C. until the content solution was approximately 100 L visually. And, the residue was left standing still under a nitrogen atmosphere and at an internal temperature of 30° C. or lower until activated carbon filtration of the second batch was finished.

As a second batch, the same operation as described above was carried out. The filtrate and washes of the second batch were added to the 500 L reactor 1 to be pooled with the residue of the first batch, and concentration under a reduced pressure was started. Under hot water circulation at 60 to 70° C., when the distillate outflow had weakened, toluene (144 kg) was added thereto, then, again, under hot water circulation at 60 to 70° C., concentration under a reduced pressure was carried out until distillate outflow weakened. At this point, the residue was analyzed and the toluene/target product ratio (0.167 w/w) was calculated from the di-tert-butyl [3-(3-{4[(pyridin-2-yloxy)methyl]benzyl}isoxazol-5-yl)pyridin-2-yl]imido dicarbonate content and the toluene content in the concentration residue. Toluene (29.66 kg, corresponding to a toluene/target product ratio of 0.700 w/w) was added thereto, the solution was stirred at an internal temperature of from 15 to 30° C. for 30 minutes or longer, so as to obtain a toluene solution of title compound (containing 42.37 kg of the target product; yield: 74.7%).

HPLC conditions: column: CAPCELL PAK C18 MGII (5 μm, 150×4.6 mml.D., SHISEIDO), mobile phase: acetonitrile/water/trifluoroacetic acid=180/820/1 to 900/100/1 (v/v/v).

Example 27

3-(3-(4-pyridin-2-yloxymethyl)-benzyl)-isoxazol-5-yl)-pyridin-2-ylamine

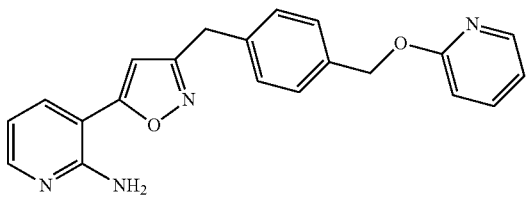

To a toluene solution of di-tert-butyl [3-(3-{4[(pyridin-2-yloxy)methyl]benzyl}isoxazol-5-yl)pyridin-2-yl]imido dicarbonate (containing 42.37 kg (75.85 mol)) was added formic acid (181 kg, 4.27 w/w) dropwise at an internal temperature of from −5 to 20° C., which was stirred at an internal temperature of from 22 to 32° C. for 19 to 20 hours. After the end of the reaction was confirmed by HPLC analysis, the internal temperature was cooled to −5 to 10° C. and the content solution was divided into two fractions and added to the 500 L reactors 1 and 2, respectively.

For the 500 L reactor 1, post-processing was carried out as described below. Under stirring, water (74 kg, 1.75 w/w) was added thereto dropwise at an internal temperature of from −5 to 20° C., further, tert-butylmethylether (31.4 kg, 0.74w/w) and n-heptane (29.0 kg, 0.684 w/w) were added thereto at an internal temperature of from 0 to 25° C. The solution was stirred at an internal temperature of from 15 to 25° C. for five minutes, left standing still for 30 minutes or longer to separate the lower layer. The lower layer was returned to the reactor, tert-butylmethylether (31.4 kg, 0.74 w/w) and n-heptane (29.0 kg, 0.684 w/w) were added thereto again at an internal temperature of from 0 to 25° C., the solution was stirred at an internal temperature of from 15 to 25° C. for five minutes, then, left standing still for 30 minutes or longer, and the lower layer was separated again. The lower layer was returned to the reactor and, first, an aqueous solution of 48% sodium hydroxide (116 kg; 1392.0 mol, 18.35M/M as sodium hydroxide) was added dropwise at an internal temperature of from 0 to 25° C. Next, at the same temperature range, ethyl acetate (96 kg, 2.26 w/w) was added thereto and an aqueous solution of 48% sodium hydroxide (20.5 kg; 246.0 mol, 3.24M/M as sodium hydroxide) was added thereto dropwise. In addition, herein, at same temperature range, an aqueous solution of approximately 8% sodium hydroxide (mixed solution of an aqueous solution of 48% sodium hydroxide (12.7 kg; 152.4 mol, 2.00M/M as sodium hydroxide) and water (64 kg, 1.5 w/w)) was added thereto dropwise until a pH of the lower layer was pH 8.00 to 9.00, (actual value: pH 8.58) (0.75 kg used). Thereafter, the solution was stirred for one hour or longer at an internal temperature of from 20 to 30° C. and left standing still overnight, then, the pH of the lower layer was checked again (actual value: pH 8.29) and the lower layer was eliminated. To the upper layer remaining in the reactor was added an aqueous solution of approximately 5% sodium bicarbonate (mixed solution of sodium bicarbonate (5.3 kg, 63.09 mol) and water (101 kg, 2.375 w/w)), which was stirred at an internal temperature of from 20 to 30° C. for one hour or longer and then left standing still for 30 minutes or longer. After the lower layer (pH8.60) was eliminated, to the upper layer was added water (106 kg, 2.5 w/w), which was stirred at an internal temperature of from 20 to 30° C. for one hour or longer, then, left standing still for 30 minutes or longer, and the lower layer (pH7.17) was eliminated again.

For the 500 L reactor 2, the same post-processing was carried out concurrently with the 500 L reactor 1.

The content solution of the 500 L reactor 1 was transferred to the 500L reactor 2 and concentrated under a reduced pressure under hot water circulation at 55 to 65° C. until the content solution was approximately 100 L. Next, to the concentration residue were added ethanol (42 kg, 1.0 w/w) and ethyl acetate (96 kg, 2.26 w/w), which was stirred for five minutes, then, concentrated under a reduced pressure under hot water circulation at 55 to 65° C. until a level of the reduced pressure of −0.092 MPa or greater and almost no distillate outflow was observed. At this point, as precipitation of crystal was observed, ethyl acetate was added little by little until the crystal dissolved completely (13.85 kg used). After ethanol (18.3 kg) and ethyl acetate (6.7 kg) were further added, the internal temperature was adjusted to 50 to 55° C., and after confirming visually that the crystal was dissolved, n-heptane (33.5 kg, 0.79 w/w) was added thereto over 30 minutes or longer at an internal temperature of from 45 to 55° C. Then, after 3-(3-(4-pyridin-2-yloxymethyl)-benzyl)-isoxazol-5-yl)-pyridin-2-ylamine (0.011 kg), which can be synthesized according to the methods described in the pamphlet of the International Publication WO 08/136279, Specifications, Example 18, was added thereto at an internal temperature of from 45 to 50° C. and precipitation of crystal was observed, the solution was stirred at the same temperature range for one hour or longer. After n-heptane (66.9 kg, 1.58 w/w) was added dropwise over one hour or longer at an internal temperature of from 45 to 55° C., the internal temperature was cooled to 0 to 10° C. over four hours or longer, and the solution was stirred at the same temperature range for five hours or longer. After the content solution was sampled and it was confirmed that the rate of crystallization of the target product was 94%, the suspension was filtered under pressure, the crystal was pour-washed in the order with mixed solution of ethanol-ethyl acetate-n-heptane (mixed solution of ethanol (3.60 kg, 0.085 w/w), ethyl acetate (4.15 kg, 0.098 w/w) and n-heptane (18.81 kg, 0.444 w/w)), and mixed solution of ethanol-n-heptane (mixed solution of ethanol (7.25 kg, 0.171 w/w) and n-heptane (18.81 kg, 0.444 w/w)) to obtain a wet crude crystal of the title compound (36.52 kg) as a slightly yellow crystal.

The obtained wet crude crystal of 3-(3-(4-pyridin-2-yloxymethyl)-benzyl)-isoxazol-5-yl)-pyridin-2-ylamine (36.52 kg) and ethanol (57.9 kg, 2.37 w/w) were added sequentially to a 500 L dissolution can, which was nitrogen-substituted beforehand, and heated to an internal temperature of from 70 to 75° C. to dissolve the crystal. While maintaining the temperature, this dissolution solution was transferred through a SUS filter to a 500 L crystallization can, and the 500 L dissolution can and SUS filter were washed thoughtly with ethanol (19.3 kg, 0.8 w/w) which was kept heated at an external temperature of approximately 65° C. Next, the filtrate was adjusted to an internal temperature of from 55 to 60° C., and it was confirmed that the solution inside the can was homogenous. Thereafter, when the internal temperature was cooled slowly to 48 to 51° C., crystal precipitated. After heating again to an internal temperature of from 55 to 60° C. to dissolve the crystal, immediately the internal temperature was cooled to 48 to 51° C. and 3-(3-(4-pyridin-2-yloxymethyl)-benzyl)-isoxazol-5-yl)-pyridin-2-ylamine (0.011 kg), which can be synthesized according to the methods described in the pamphlet of the International Publication WO 08/136279, Specifications, Example 18, was added immediately. Then, after precipitation of crystal was confirmed visually at an internal temperature of from 45 to 50° C., the suspension was stirred at an internal temperature of from 43 to 47° C. for one hour to one hour and 30 minutes, and the internal temperature was cooled to 0 to 10° C. over four hours or longer. At this point, after a precipitated crystal was sampled and the crystal form thereof was confirmed to be identical to the reference sample, the suspension was stirred overnight at the same temperature range. On the next day, after the crystal form was confirmed to be identical to the reference sample, the crystal was solid-liquid separated with a centrifuge divided in two times, and respectively pour-washed with approximately half of the amount of 19.3 kg of ethanol to obtain a wet crystal of the target product (24.23 kg). This wet crystal was placed into a mixed type vacuum dryer and dried under a reduced pressure at an external temperature of from 20 to 30° C. for 6 hours or longer and an external temperature of from 35 to 45° C. for 12 hours or longer, so as to obtain the title compound (23.52 kg, 65.63 mol, yield: 86.8%) as a pale yellow crystal.

$^1$H-NMR Spectrum (CDCl$_3$)δ(ppm):4.07(2H,s), 5.37(2H,s), 5.42(2H,brs), 6.25(1H,s), 6.71(1H,dd,J=5.2,7.6 Hz), 6.80 (1H,d,J=8.4 Hz), 6.87-6.91(1H,m), 7.30(2H,d,J=7.6 Hz), 7.44(2H,d,J=7.6 Hz), 7.56-7.61(1H,m), 7.70(1H,dd,J=2.0, 7.6 Hz), 8.14(1H,dd,J=2.0,4.8 Hz), 8.16-8.19(1H,m).

HPLC conditions: column: CAPCELL PAK C18 MGII (5 µm, 150×4.6 mm I.D., SHISEIDO), mobile phase: acetonitrile/water/trifluoroacetic acid=180/820/1 to 900/100/1 (v/v/v).

Industrial Applicability

According to the manufacturing method of the present invention, there is provided an efficient method for manufacturing heterocycle-substituted pyridine derivatives, and the industrial applicability is that heterocycle-substituted pyridine derivatives can be manufactured on an industrial scale.

We claim:

1. A method for manufacturing a compound represented by the following formula (1):

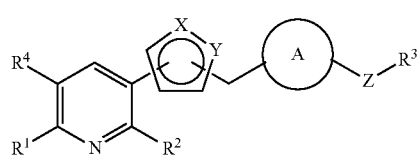
(I)

the method comprising reacting a compound represented by the following formula(III):

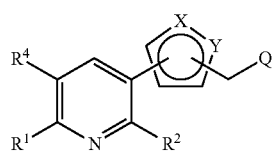
(III)

and a compound represented by the following formula (II):

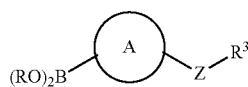
(II)

in a solvent and in the presence of a palladium catalyst and a base, wherein

R$^1$ represents a hydrogen atom;

R$^2$ represents an amino group that may be protected with a protective group selected from acetyl, pivaloyl and tert-butoxycarbonyl;

X represents an oxygen atom and Y represents a nitrogen atom;

Q represents a leaving group selected from halogen, a para-toluenesulfonyloxy group, a benzylsulfonyloxy group, methanesulfonyloxy group, a trifluoromethanesulfonyloxy group, and a chloromethanesulfonyloxy group;

the ring A represents a benzene ring;

Z represents —CH$_2$O—;

R represents a hydrogen atom or a C$_{1-6}$ alkyl group, if the two R groups are both C$_{1-6}$ alkyl groups, they together form a ring;

R$^3$ represents pyridinyl; and

R$^4$ represents a hydrogen atom.

2. The manufacturing method according to claim 1, wherein the Q in the above formula (III) represents a halogen atom or a substituted sulfonyloxy group selected from a para-toluenessulfonyloxy group a benzylsulfonyloxy group, methanesulfonyloxy group, a trifluoromethane-sulfonyloxy group, and a chloromethanesulfonyloxygroup.

3. The manufacturing method according to claim 1 or 2, wherein a partial structure represented by:

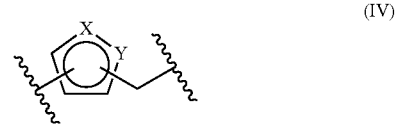
(IV)

in the above formula (I) is the following partial structure:

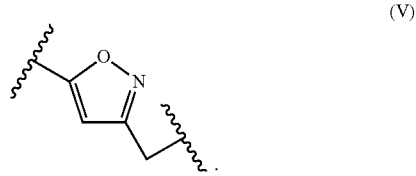 [SMILES: *Cc1cc(*)on1]
(V)

4. The manufacturing method according to claim 1, wherein when the R$^2$ is an amino group that may be protected protective group selected from acetyl, pivaloyl and tert-butoxycarbonyl, the method further comprises deprotecting the protective group by an acid or a base.

5. The manufacturing method according to claim 1, wherein the compound represented by the following formula (III):

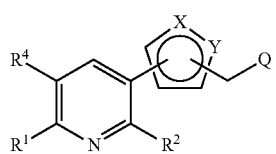
(III)

is manufactured by a manufacturing method comprising the steps of subjecting a compound represented by the following formula (VI):

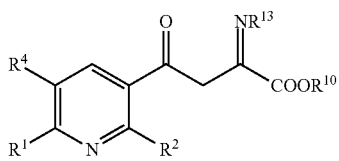

(VI)

to a cyclization reaction;
performing a reduction reaction; and
performing halogenation thereafter, (wherein. $R^1$, $R^2$, $R^4$, X, Y, and Q are defined the same as above, $R^{10}$ represents a $C_{1-6}$ alkyl group, and $R^{13}$ represents a hydroxyl group).

6. The manufacturing method according to claim 5, wherein when the $R^2$ represents an amino group having a protective group selected from acetyl, pivaloyl and tert-butoxycarbonyl, the method further comprises deprotecting the protective group by an acid or a base after the reduction reaction.

7. The manufacturing method according to claim 5, wherein when the $R^2$ represents an amino group, the method further comprises protecting the amino group.

* * * * *

UNITED STATES PATENT AND TRADEMARK OFFICE
CERTIFICATE OF CORRECTION

PATENT NO. : 8,410,277 B2
APPLICATION NO. : 12/809011
DATED : April 2, 2013
INVENTOR(S) : Jun Niijima et al.

It is certified that error appears in the above-identified patent and that said Letters Patent is hereby corrected as shown below:

ON THE TITLE PAGE:

At item (73), Assignee, change "Eisai R&D Managment Co., Ltd., Tokyo (JP)" to -- Eisai R&D Management Co., Ltd., Tokyo (JP) --.

Signed and Sealed this
Twenty-third Day of July, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,410,277 B2 | Page 1 of 1 |
| APPLICATION NO. | : 12/809011 | |
| DATED | : April 2, 2013 | |
| INVENTOR(S) | : Niijima et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 168 days.

Signed and Sealed this
Fourth Day of February, 2014

Michelle K. Lee
*Deputy Director of the United States Patent and Trademark Office*